US012638352B2

(12) United States Patent
Smits et al.

(10) Patent No.: US 12,638,352 B2
(45) Date of Patent: May 26, 2026

(54) CLOSED CELL PRESSURE SENSOR

(71) Applicant: Nederlandse Organisatie voor toegepast-natuurwetenschappelijk onderzoek TNO, 's-Gravenhage (NL)

(72) Inventors: Edsger Constant Pieter Smits, Eindhoven (NL); Gerardus Titus Van Heck, Eindhoven (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 325 days.

(21) Appl. No.: 18/293,944

(22) PCT Filed: Aug. 4, 2022

(86) PCT No.: PCT/NL2022/050458
§ 371 (c)(1),
(2) Date: Jan. 31, 2024

(87) PCT Pub. No.: WO2023/014223
PCT Pub. Date: Feb. 9, 2023

(65) Prior Publication Data
US 2025/0076139 A1　　Mar. 6, 2025

(30) Foreign Application Priority Data

Aug. 5, 2021　(EP) .................................... 21189909

(51) Int. Cl.
*G01L 9/00*　　(2006.01)
*A61B 5/00*　　(2006.01)
(52) U.S. Cl.
CPC ............ *G01L 9/0072* (2013.01); *A61B 5/447* (2013.01); *G01L 9/0051* (2013.01); *A61B 2562/0247* (2013.01)

(58) Field of Classification Search
CPC ....... G01L 9/0072; G01L 9/0051; G01L 1/02; A61B 5/447; A61B 2562/0247
See application file for complete search history.

(56) References Cited

U.S. PATENT DOCUMENTS

2009/0056465 A1　3/2009　Nakamura
2016/0363490 A1 *　12/2016　Campbell ................. G01L 1/18
(Continued)

FOREIGN PATENT DOCUMENTS

CN　　100999079 A　　7/2007
CN　　104040315 A　*　9/2014　........... G01L 9/0042
(Continued)

OTHER PUBLICATIONS

European Patent Office, International Search Report in corresponding International Application No. PCT/NL2022/050458 dated Nov. 21, 2022.

*Primary Examiner* — Thomas M Hammond, III
(74) *Attorney, Agent, or Firm* — Leydig, Voit & Mayer, Ltd.

(57) ABSTRACT

A system for measuring external force is described. The system includes a substrate forming a set of closed pockets having at least a flexible wall deforming as a function of the external force and an enclosed MEMS device configured to cause variation of an electric signal as a function of a pressure inside the pocket. The flexible wall is provided with an outwards protruding shape configured to flex inwards into the pocket in a presence of the external force and to recover the outwards protruding shape absent the external force.

21 Claims, 15 Drawing Sheets

(56) References Cited

U.S. PATENT DOCUMENTS

2017/0135417 A1 *  5/2017  Lucrecio ................... G01L 1/00
2022/0341803 A1 * 10/2022  Budgett ............... G01L 27/005

FOREIGN PATENT DOCUMENTS

| CN | 105606265 | B |   | 7/2018 | |
| CN | 108871656 | A | * | 11/2018 | ............ G01L 11/002 |
| DE | 3502275 | A1 |   | 7/1986 | |

* cited by examiner

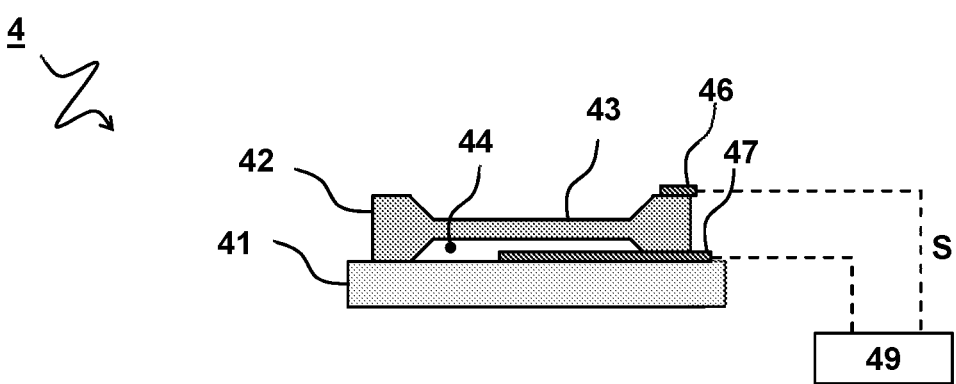
FIG 6A
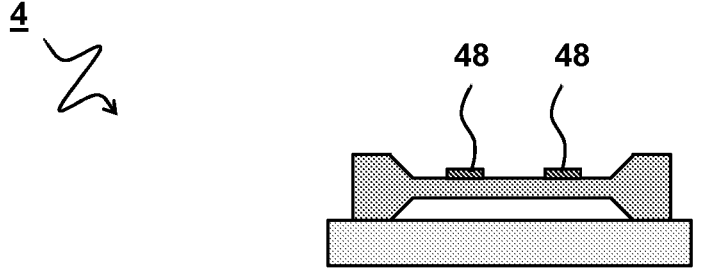
FIG 6B
FIG 6C

CLOSED CELL PRESSURE SENSOR

CROSS-REFERENCE TO RELATED APPLICATIONS

This patent application is a U.S. National Phase of PCT International Application No. PCT/NL2022/050458, filed Aug. 4, 2022, which claims priority to European Application No. 21189909.1, filed Aug. 5, 2021, which are both expressly incorporated by reference in their entireties, including any references contained therein.

TECHNICAL FIELD AND BACKGROUND

The present disclosure generally relates to forces sensors and systems for measuring an external force. More in particular, the disclosure relates to a system comprising a substrate, preferably a flexible substrate, forming a set of closed pockets having at least a flexible wall with an outwards protruding shape deforming as function of the external force with an enclosed pressure sensor for determining a change of pressure in response to the external force. In addition the present disclosure relates to a method of manufacturing said system.

There are many reasons to measure force and/or pressure exerted onto or by a body part. In the medical or diagnostic domain applications include measuring external pressure or force, e.g. distribution.

Known measuring modes include traditional pressure and force sensors such as strain gauges, loadcells and manometers, such as digital manometers, which are based on strain gauges. While generally accurate such sensors are bulky, hard to miniaturize, and typically expensive.

Microelectromechanical systems (MEMS)-based pressure sensors have recently gained acceptance as low-cost alternatives for measuring air pressure. The flexible membrane, e.g. a back-etched silicon membrane, with read-out electronics disposed thereon as comprised in MEMS devices offers high accuracy for air pressure monitoring but is generally too fragile to withstand direct contact from an external force. In addition, MEMS-pressure sensors typically measure only very locally.

WO9736156A1 discloses what is known as an air pack-type contact pressure measuring method and system. The system includes an inflatable sensor pouch. The exit pressure is measured with a barometric sensor. EP2873368A1A discloses a device for bedding for sleep monitoring that is based on similar principles and that includes inflatable sensor pouches. Disadvantageously, the such systems require an external pump and/or pneumatic tubing to inflate the pouches making the systems expensive, heaving and/or cumbersome to use. Without regular or even continuous reinflation deflation of the pouches means short operational lifetime, typically below 1 or 2 minutes, and/or reduced system performance.

CN105606265 concerns a hydraulic-pressure-conducting-based flexible touch sensor for grip sensing in an artificial limb or robot hand. The sensor comprises a metal pedestal and a plurality of isolated sealed oil filled cavities that transduce an externally applied pressure to a pressure sensitive unit.

US2017009064 discloses an encapsulated pressure sensor that includes a MEMS-based pressures sensor on a mounting substrate that is encapsulated by a dome-shaped rubber member that surrounds the pressure sensor. The disclosed combination of rigid support substrate, MEMs-based pressure sensor, and rubber dome allows sensing an applied force at a single point of contact between stylus or robot gripping arm and an external surface.

Flexible sensors, e.g. resistive or capacitive based, whereby electrodes are provided along polymer membranes bounding opposing faces of closed cell offer a cost-effective and scalable alternative to conventional pressure sensors. However, disadvantages include reduced linearity, sensitivity, and/or accuracy, which are believed to be related to viscoelastic deformations of the electrodes and/or a generic dependence of the response on the direction and position of the applied force.

SUMMARY

Aspects of the present disclosure relate to a system for measuring external force. The system comprises a flexible substrate forming a set of closed pockets, each pocket having at least one flexible wall deforming as function of the external force. The system further comprises a set of MEMS devices, each configured to cause variation of an electric signal as function of a pressure inside a respective pocket. Variation of the electric signal can be understood as a response of an electrical circuit comprises in the MEMS device, such as but not limited to change in electrical resistance, a change in capacitance and/or a change in inductance. Advantageously, the flexible wall is provided with an outwards protruding shape that is configured to flex inwards into the pocket for increasing the pressure inside the pocket in presence of the external force and provided with a resilient means configured to recover the outwards protruding shape absent the external force. Additionally a fluid is provided within the pocket. Accordingly, a difference between the electric signal as a result of the hydrostatic pressure of the fluid in presence of the external force the signal in absence of the external force correlates to the external force. The protruding shape can advantageously serve as an outermost contact point for interaction, e.g. with objects approaching and contacting the device and/or changing environmental pressures. Since the shape protrudes, with respect to the pocket, the effect of direction on the incoming force onto the pocket is reduced, in particular in comparison to force sensors comprising a pocket bound by a planar flexible wall where sensor response was found to depend on the angle and/or position at which the incoming force presses onto the pocket.

In a preferred embodiment, the resilient means is provided by the flexible wall that comprises, or essentially consists of, a shape recovering resilient composition that is configured to recover the outwards protruding shape absent the external force. Providing the resilient means by the flexible wall advantageously allows restoring the protruding shape, restoring the pocket wall to a quiescent state, absent the external force without additional means, e.g. external means such as a spring.

The resilient means thus mitigates deformation of the pocket e.g. due to partial deflation via interstitial pores in the wall(s), even after prolonged exposure to increased pressure. In contrast conventional air packs require external means for reinflation/recovery to an initial state after use.

Preferably, the flexible substrate comprises, or essentially consists of, an elastomeric composition, such as a thermoplastic elastomer composition. The flexible substrate may consist of one or more thermoplastic elastomer composition. Advantageously, a flexible substrate comprising of an elastomeric composition allows conforming the substrate, and ideally the system, to an outer perimeter of a target object, e.g. a flexible or elastomeric object such as a body part.

Preferably, the flexible wall comprises, or is essentially formed of, a thermoplastic elastomer composition having essentially elastomeric properties at normal operating temperature of about 25° C. of the system and thermoplastic properties at a temperature well above a normal operating temperature range. As will be explained hereinbelow in more detail use of compositions having essentially elastomeric properties at a temperature within a normal operating range while having thermoplastic properties at a temperature well above the normal operating range improves manufacturability of the device.

In another or further preferred embodiment, a predominant portion of the exterior surface of the outwards protruding shape extends in a direction essentially parallel to the base layer. Essentially parallel is considered to include deviations from a parallel configuration of less than ±10°, preferably less than ±5°, more preferably less than ±2°. The parallel portion is greater than 80%, preferably greater than 85%, or even more preferably greater than 90% of the total exterior surface area of the shape. By providing an essentially flat contact area, an external force exerted on the outwards protruding shape may be distributed over a larger interaction area when compared to, for example, a point contact in the of a dome shaped protrusion. This allows the outward protruding shape to flex more uniformly, which mitigates effects of the material's mechanical properties on the resulting pressure perceived by the sensor, and thereby improves accuracy/linearity of received pressure readings.

In a strongly preferred embodiment, the pocket comprises a main volume in fluid connection to an adjacent volume that protrudes sideways from the main volume, wherein the outwards protruding shape in the flexible wall is formed exclusively above the main volume and the MEMS device is at least in part, preferably completely, disposed in the adjacent volume. Positioning the MEMS device at least party, preferably completely, in a sideways protruding volume away from a main volume below the protruding shape protects the MEMS device, in use, e.g. due to, a direct contact with an inwardly flexing portion of the protruding shape. Avoiding contact between the an inwardly flexing portion of the protruding shape and the MEMS device improves a haptic experience of an end user pressing down, e.g. with a finger, onto the protruding shape. Avoiding contact between the MEMS device and the protruding shape mitigates potential contact damage to the MEMS device, e.g. during a complex or maximum inward depression of the protruding shape.

In other or further preferred embodiments, the substrate comprises, or is essentially formed of, a stack of two or more sheets, preferably each of a flexible material, including a first sheet forming a sensing layer of the substrate that includes the flexible wall, and a second sheet forming a base layer opposite the sensing layer, whereby the pockets are formed between the sensing layer and the base layer. Forming the substrate of flexible materials, e.g. elastomeric materials, allows conforming the substrate to an outer perimeter of a target object, e.g. a flexible or elastomeric object such as a body part.

Preferably, the stack includes a structured intermediate sheet forming a spacer structure between the sensing layer and the base layer with an upstanding wall structure. The wall structure advantageously forms sidewalls that laterally bound the pockets and separates pockets from adjacent ones. providing the spacer structure that defines an upstanding wall structure that laterally bounds the pocket provides additional range for inwards flexing of the protruding shape. Increasing the range for inward flexing of the protruding shape further mitigates incidental contact between opposing walls of the pocket. In a preferred embodiment, the spacer structure is formed from one or more sheets, preferably a single sheet, patterned to include a structure of laterally separated apertures or cut-outs, each defining an upstanding wall structure that laterally bounds an individual pocket. Alternatively the spacer structure may be formed by additive manufacturing methods. Yet further alternatively the sensing top layer, with protruding shapes, may be glued to or directly connected, e.g. bonded, to the base layer, whereby individual pockets are laterally bound and separated from adjacent pockets by a bonding or gluing structure following a perimeter of the pocket.

In strongly preferred embodiments the adjacent volume is formed in the sidewall of the pocket. For example, in one embodiment, the main volume and the adjacent volume of each pocket can advantageously be defined by corresponding apertures provided in a spacer sheet.

As evident from the present specification and the accompanying drawings the presently presented system can be of particular benefit for medical sensing applications, e.g. for measuring a force or pressure applied onto the skin of a part of a body, in particular a human body, or a pressure between a body part and product in contact therewith.

In preferred embodiment, the sensing layer, the base layer, and/or the intermediate layer are each formed of an individual, single, plastic film, preferably an elastomeric or rubbery film. Forming the substrate of single plastic films simplifies manufacturing and/or particular structural integrity of the substrate, in particular during manufacturing, as opposed assembling individual pockets from separate wall pieces. Optionally the base layer can be a part or a portion of the sensing layer, e.g. by a fold.

Preferably, the MEMS devices and/or electronic wiring for interfacing with each of the MEMS devices are disposed along the base layer. Providing the wiring along the base layer simplifies manufacturing and reduces potential bending and/or stretching stresses onto the wiring during use of the system. More preferably the electrical circuitry for each of the MEMS devices is provided along a trajectory between adjacent ones of the pockets, most preferably example at locations where it is covered by the spacer structure. Positioning the wiring, circuitry, along the contours of the pockets, preferably under the spacer structure, puts the wiring away from parts of the walls having the largest deformations during use, and thus further mitigates bending and/or stretching stress on the wiring, in particular in presence of the external force.

In some embodiments, the base layer is provided with an outwards protruding shape that is configured to flex inwards into the pocket for increasing the pressure inside the pocket in the presence of the external force and provided with a resilient means configured to recover the outwards protruding shape absent the external force, forming a second sensing layer opposite the first. Thus the system can advantageously be configured to response to external forces impacting onto the pocket from opposite direction.

In some preferred embodiments, the system comprises a reference pressure sensor. Advantageously the reference sensor can be configured to measure an ambient pressure, e.g. an air pressure, outside the closed pocket. The response from the reference sensor can advantageously serve as a reference or correction signal for the electric signal from the MEMS device inside the pocket. Thus the system can advantageously correct for variations in ambient pressure, e.g. due to changes in altitude, weather conditions, and/or external air flows impacting onto the pocket. The reference pressure sensor may in principle be positioned at any location outside the pocket, for example along an exterior face of a pocket, between pockets, or by a support carrying the system. Alternatively or additionally the system may be configured to interface with a remote or external reference sensor. For example, the reference sensor may be a remote sensor, e.g. a pressure sensor such as an altimeter, of a mobile device such as a smart phone.

Accordingly, in a preferred embodiment, the system is configured to receive a reference pressure from an external device, preferably a mobile device, upon initial pairing with such external device. Alternatively, or in addition, the reference pressure can be extracted from a database such as a web-based service, for example based on GPS coordinates. Advantageously mobile devices, such as handheld like a phone, or a smart watch, having an integrated barometric pressure sensor are widely available.

According to other of further aspects of the present disclosure concerns a method of manufacturing the system according to the invention. The method comprises providing a set of MEMS devices inside a respective one or more closed pockets formed by a substrate, each pocket having at least one flexible wall deforming as function of an external force applied to the flexible wall, each MEMS device configured to cause variation of an electric signal as function of a pressure inside the respective pocket, wherein the flexible wall is provided with an outwards protruding shape configured to flex inwards into the pocket for increasing the pressure inside the pocket in presence of the external force and provided with a resilient means configured to recover the outwards protruding shape absent the external force.

In a preferred embodiment, the resilient means is provided by the flexible wall comprising a shape recovering resilient composition configured to recover the outwards protruding shape absent the external force.

Typically, the substrate comprises a stack of two or more sheets, preferably flexible sheets. Preferably, the sheets comprise or essentially consist of a thermoplastic elastomer composition.

In a preferred embodiment, the substrate is formed by stacking two or more sheets including a first sheet forming a sensing layer of the substrate that includes the flexible wall, and a second sheet forming a base layer opposite the sensing layer, whereby the pockets are formed between the sensing layer and the base layer.

Preferably, the stack includes an intermediate layer forming a spacer structure between the sensing layer and the base layer with an upstanding wall structure forming sidewalls that laterally bound the pockets and separates pockets from adjacent ones Generally, the method comprises providing electronically conductive wiring for interfacing with the MEMS devices. Preferably, the MEMS devices and electronic wiring for interfacing with each of the MEMS devices are disposed along the base layer.

In a preferred embodiment, forming the substrate comprises laminating the sheets to respective opposing sheets along outer perimeters of the respective pockets. Alternatively the layers may be glued together.

In another or further preferred embodiment, the flexible wall is formed in a step comprising thermoforming portions of the sensing layer at positions in correspondence with the respective pockets.

In a preferred embodiment, disposing the wiring comprises printing an ink comprising electrically conductive filler material and an elastomer matrix material or precursor thereto.

The spacer layer can in principle be provided using any suitable manufacturing method, including but not limited to machining and additive manufacturing. In a preferred embodiment, manufacturing the spacer layer comprises machining through holes so as to define upstanding wall structures forming sidewalls that laterally bound the pockets and separates pockets from adjacent ones. Machining can include methods including but not limited to cutting, laser cutting, and molding. Alternatively the spacer may be formed by additive manufacturing methods.

In a preferred embodiment, the upstanding wall structure further defines an adjacent volume protruding sideways from a main volume, wherein the outwards protruding shape in the flexible wall is formed exclusively above the main volume and the MEMS device is at least in part, preferably completely, disposed inside the adjacent volume.

In some embodiments, the base layer is provided with an outwards protruding shape configured to flex inwards into the pocket for increasing the pressure inside the pocket in the presence of the external force and provided with a resilient means configured to recover the outwards protruding shape absent the external force, forming a second sensing layer opposite the first.

As will be understood for the specification as a whole the system according to the invention offers a large number of advantages.

Compared to the traditional air sac sensors present system includes localized MEMS pressure sensors. Due to this local transduction there is no need to output pneumatic pressure, obviating a need for tubing to convey pneumatic pressure from the pocket to an external sensor. In addition means like pumps to (re) inflate the pocket are omitted because the pocket is essentially closed.

Inventors found that the ability to digitize signals allowed multiplexing a plurality of sensors in an array form in a comparatively convenient way.

Advantageously the pocket, walls and layers can comprise or essentially consist of thermoplastic elastomeric materials, like TPU, allowing the system to be flexible, deformable without essentially losing functionality. Advantageously the system can be conformable. Preferably the system can have a bend radius, measured to the inside curvature, without essentially losing functionality of below 5 cm, preferably less, e.g. ≤2 cm or ≤1 cm, e.g. in a between 0.5 and 1 cm. Allowing the system to be formable onto curved surfaces making the system useful determine pressure distributions along soft and/or curved surfaces. For example, the system can be bent over body parts, including but not limited to the chest, arm and an leg.

The system can advantageously be used to measure external forces (and/or distribution thereof) exerted on to an object of interest. Alternatively or additionally the system according to the invention can be used to measure forces (and/or distribution thereof) exerted onto the system by or from within the object of interest.

Inventors found that the system can reliably detect pressure variations. In particular inventors found that the system can accurately and linearly measure pressures over a broad range, whereby the operational range can generally be determined by an operational range of the MEMS comprised in the device, such as but not necessarily limited to 20 Pa-10 kPa.

In some preferred embodiments, the system comprises a wireless tag. Where the wireless tag contains a microcontroller, a power supply such as a battery, and radio IC. The tag advantageously enables that the data of sensor may be streamed or logged on or from the tag to another device, said phone, tablet or dedicated portable device using a defined wireless protocol such as Bluetooth, NFC or WIFI. In another aspect the sensor tag may stream the information directly to a local or remote server. In such implementation protocols such as WIFI, Lora, Sigfox or Zigbee may be utilized.

Advantageously, as the sensors are low power, they may be used in conjunction with energy harvesting. In particular wireless and batteryless tags may be realized that can be inductively coupled to provide power as well as data communication using NFC.

Advantageously the system can be used to monitor vital signs such as heart rate and/or breathing rate.

Accordingly, in some aspects the present disclosure concerns a textile, garment or clothing product comprising the system according to the invention. For example a shirt, bra, shorts, headband or belt comprising the system as disclosed herein.

According to another or further aspect the present disclosure concerns a diagnostic or personal monitoring product comprising the system as disclosed herein. The diagnostic product can advantageously be used to measure a sign, e.g. a vital sign, or conduction, of a mammal, e.g. a human. In a preferred embodiment, vistal sign includes a respiration and heart rate of an infant or neonate.

Said product may be in the form of wearable, like a band, clothing textile or garment. In some embodiments the product is in a form of a compression bandage, e.g. a medical compression bandage (MCB), or an underlayment for a compression bandage, comprising the system as disclosed or an assembly comprising a compression bandage and a system disclosed herein. The underlayment can be positioned between the skin of a subject and the MCB or any other means or surface exerting pressure onto the skin. The system can advantageously be in direct contact with the skin of the subject, e.g. without a need for cushioning layers because the substrate is conformable, flexible and/or since the MEMS devices are protected from a directed reach/ contact. Or course it will be understood that further intermedialt layers (e.g. cushioning or wound dressing layers) can be applied.

In some embodiments the diagnostic product concerns a bed or bedding material such as a matrass, underlayments, sheets, or lining. Alternatively the diagnostic product concerns a pillow or seating product such as a chair, wheel chair, a cushion and/or lining and/or underlayment for said pillow or seating product.

Said product can for example be used to advantage to monitor a pressure between said product and a body part. For example, for the treatment of pressure ulcers also known as pressure sores or bed sores, which are generally considered to relate to localized damage to the skin and/or underlying tissue that usually occur over a bony prominence as a result of usually long-term pressure, or pressure in combination with shear or friction.

Advantageously the output of the device can be used to optimize bandage pressure, e.g. for persons unable to communicate. Alternatively, or in addition, the diagnostic product can be used to monitor pressure evolution as function of time. In some embodiments, the product is used to monitor/ detect swelling between a body part and a bandage. The system be by of particular use in systems for the treatment of diagnosis of conditions where swelling is treated using accurate applied pressure.

Alternatively, or in addition, the diagnostic product can be used for ballistocardiography by detecting pressure variations exerted onto the product contacting an external surface of a body part of a subject, e.g. an arm, due to motion of blood in underlying vessels. As compared to ballistocardiographic tools that use accelerometer sensors the present system is less sensitive to motion artefacts because the system is principally less sensitive to motion artefacts.

Advantageously, the product, e.g. the system or assembly, can be used for monitoring a pressure between a body part, e.g. a limb, and a bandage applied thereto, during and/or after application of the bandage, including positioning the system or assembly between the body part and the bandage and monitoring an output signal of at least one MEMS device of the system as a function of time. These output signals can be recorded and/or stored over a period of time, for later recall. Alternatively or in addition the signals may be displayed for direct use (e.g. to display an applied pressure/force and/or pressure distribution between during application of a MCB. The output signal received from a MEMS device corresponds to a pressure exerted by the bandage on the pocket wherein the MEMS device is installed. Accordingly, it can be determined whether the output signal of one or more MEMS device corresponds to an applied pressure being outside a specified pressure range. The specified pressure range can include a range of pressures suitable for compression therapy, e.g. for treatment of chronic venous disorders or lymphedema. Ideally, the specified pressure range is 10 to 70 mbar, preferably 13.33 to 66.67 mbar, which is suitable for compression therapy. Advantageously the system can be used to confirm a pressure profile as applied along a target surface, e.g. an area of skin. For example, to ensure a preferred direction of blood flow within the underlying tissue, e.g. in a direction from an extremity towards the heart.

Advantageously, the product, e.g. the system or assembly, can be used for determining a pressure distribution between a body part, e.g. a limb, and a bandage applied thereto. For example, during the step of application of a bandage along a body part and/or over a prolonged period after application of a bandage. The method includes a step of positioning the system or assembly as disclosed herein, typically an embodiment comprising a plurality of pockets arranged in an array, between the body part and the bandage, and detecting at least a first and a second output signal, of at least a first and a second MEMS device in the array. Optionally a plurality of systems (e.g. each with one pocket) may be used. Preferably, a respective output signal is detected for each of the MEMS devices. Each output signal relates to a pressure exerted on its respective pocket. Accordingly, a pressure distribution between the body part and the bandage can be determined from the output signals received, e.g by relating each output signal to the position of their respective pockets along the skin or within the array.

Advantageously, the product can be used to generate an indication or alert, e.g. to a user, if a pressure as detected is outside a specified range. Monitoring a pressure or pressure distribution between a bandage and a body part over time, e.g. when swelling of a body part is detected, when a bandage is over tensioned during the application of the bandage, or when a bandage becomes loosened from the body part.

BRIEF DESCRIPTION OF DRAWINGS

These and other features, aspects, and advantages of the apparatus, systems and methods of the present disclosure will become better understood from the following description, appended claims, and accompanying drawing wherein:

FIGS. 6A to 6C illustrate embodiments of a MEMs device comprised in the system;

FIGS. 10A to 10C illustrate embodiments of diagnostic products comprising the system;

DESCRIPTION OF EMBODIMENTS

Figure 1A:
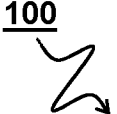
FIG. 1A illustrates an embodiment of the system in cross-section side view.

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

The basic principles underlying the system as disclosed herein will now be explained with reference to FIGS. 1A and 1B. FIG. 1A shows a partial side view of an embodiment of a system 100 for measuring an external force. The system comprises a substrate 1 that forms closed pocket 2. The pocket 2 has a flexible wall 3. The pocket is filled with a fluid, typically a gas. In addition, the system comprises a MEMS device 4. The system generally comprises a plurality, a set, of pockets and, each with one or more MEMS device configured to cause variation of an electric signal S1,S2 as function of a pressure P1,P2 inside the pocket. As used herein the term "set" may be understood to concern two or more items, typically more, e.g. three or more, ten or more or even in excess of 128.

Figure 1A:
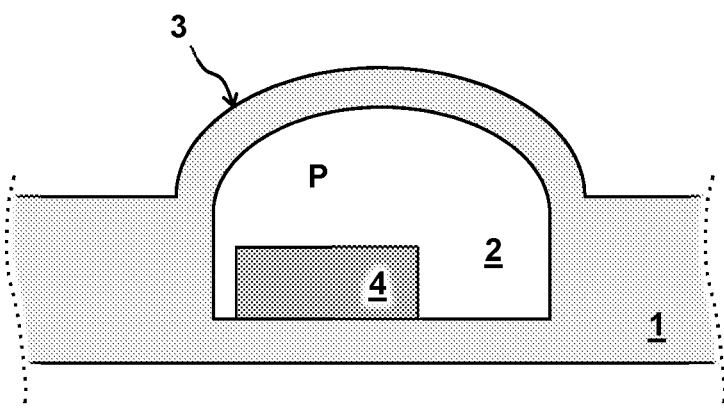
Figure 1B:
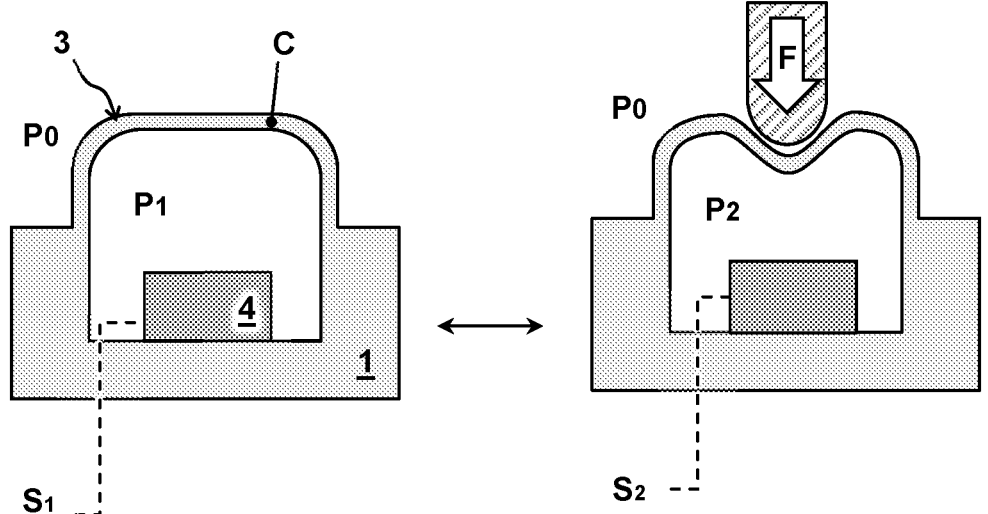
FIG. 1B illustrates an embodiment of the system in cross-section side view during a use.
Figure 2A:
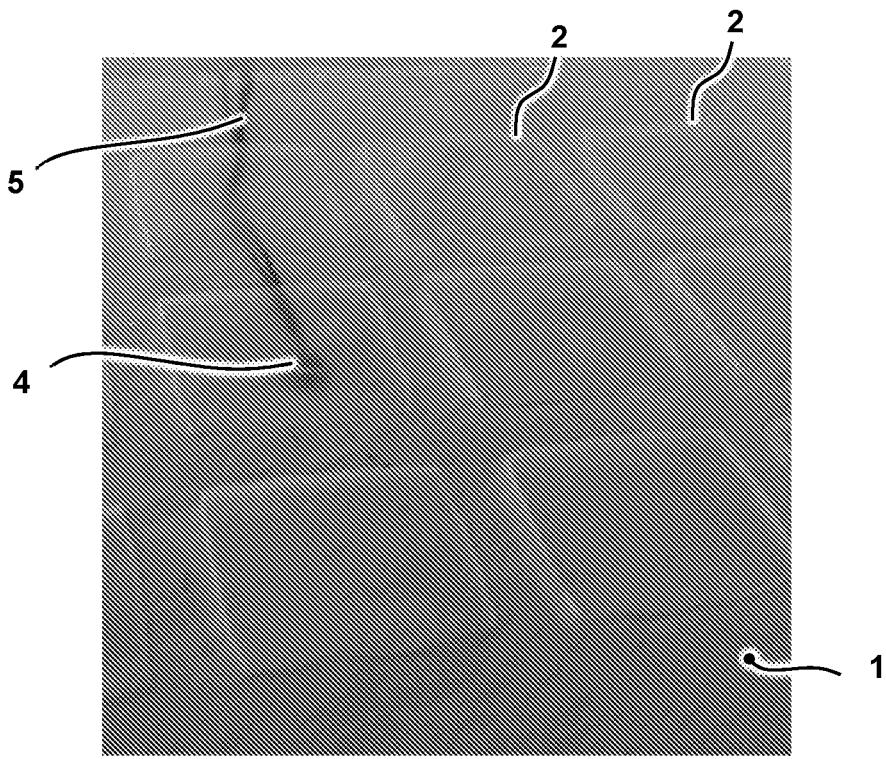
FIG. 2A is a picture of an embodiment of the system
Figure 2B:
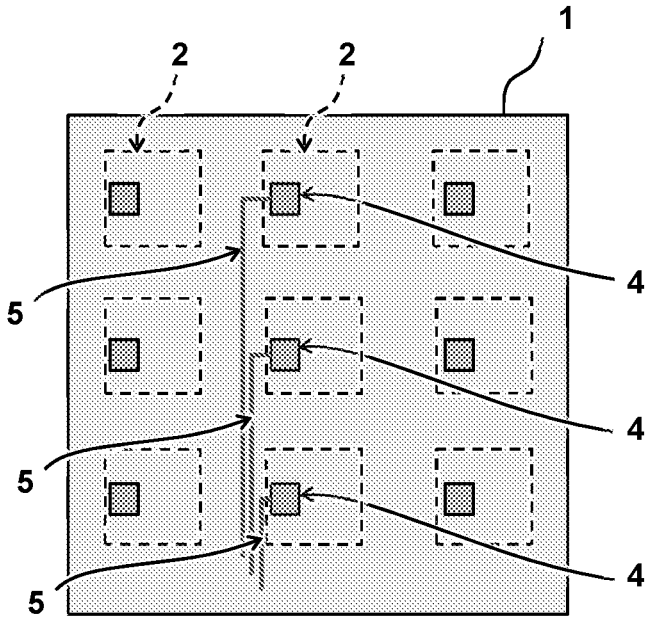
FIG. 2B illustrates an embodiment of the system in plan view.

In a preferred embodiment, e.g. as shown in FIGS. 2A and 2B the closed pockets are configured in an array, e.g. an array having M columns and N rows, wherein M and N are integers, each individually having a value of at least 1 and whereby the sum of M+N is at least 2. As shown, the pockets are arranged in an array such that a globally applied external force acting upon the system is distributed as a plurality of external forces acting upon individual ones of the pockets arranged in the array. Accordingly, configuring the pockets in an array allows for measuring a force or pressure distribution. FIG. 1 depicts a partial view of a system wherein the substrate 1 is provided with a total of nine pockets 2 configured in a 3×3 array, wherein a MEMS device 4 and accompanying circuitry 5 is provided to one of the pockets. Of course the arrangement as shown is not to be interpreted in a limiting way. Obviously, MEMS devices can be provided in multiple pockets, generally all pockets, as shown in FIG. 2B which illustrates an embodiment in plan view, whereby the circuitry 5 is positioned predominately outside a perimeter of the pockets 2.

Generally each pocket is provided with one MEMS device. It will be understood that each pocket may contain a different number of MEMS devices. Some pockets may be left empty. In some embodiments each or some of the pockets contain multiple MEMS devices, e.g. two. The sensors may be identical or configured to be responsive over difference pressure ranges. This has as advantage that the MEMS devices in a pocket may serve as back-up for each other and/or may extend a measurable detection range. However the term "set" may also be understood to refer to single elements, including systems with only a single pocket enclosing a single or plurality of MEMS devices, e.g. as shown in FIG. 1B. As compared to systems with a plurality of pockets systems with a single pocket can be more compact. The flexible wall 3 is provided with an outwards protruding shape configured to flex inwards into the pocket for increasing the pressure P inside the pocket in presence of the external force and provided with a resilient means configured to recover the outwards protruding shape absent the external force. The shape may take any suitable shape including but not limited to a dome, cone, and truncate cone. As illustrated in FIG. 1B (right) the protruding shape flexes inwardly in the presence of an external force F, e.g. an external pressure or a force induced by an external object, the protruding shape flexes inwardly, as shown in FIG. 2. Due to the resilient means the flexible wall recovers back to an initial shape (FOG 1B (right) in the absence of the external force. As will be understood the pressure inside the pocket P1, P2 scales with the external pressure P0 and force applied externally. The difference in electric signal S2-S1 scales with variations of the external pressure and force. When the external pressure is essentially constant or its contribution on changes is comparatively small relative to the external voice (preferably at least ten times smaller) a measured difference between the electric signal S2-S1 scales with the applied force.

Since the pockets are in barometric equilibrium they will not deflate when left in static situation.

The electrical circuitry 5 for each of the MEMS devices preferably comprises an electrically conductive elastomer composition. Forming the wiring of a electrically conductive elastomer composition advantageously allows the wiring allows to bend and/or flex along with the layers without losing functionality, e.g. while conforming to a curvature of an external object and/or while flexing in dependence of an applied external force. Preferably, the conductive elastomer composition has can be stretched without essentially losing functionality by a factor of at least 1.05, preferably at least 1.1, preferably more, e.g. up to 1.2 or up to 1.5. Composite compositions, e.g. inks, comprising an elastomeric matrix or precursor thereto and one or more conductive filler materials e.g. (nano)particles and/or wires at a filling ratio above a percolation threshold, were found to be particularly suitable.

In a preferred embodiment the pressure inside the pocket equals a pressure outside the pocket absent the external force within 10%, preferably within 5%, optionally within 1%, or even exactly equal within measurement tolerance. Typically the pocket is filed with air. Optionally the pocket may be filled with other gasses, e.g. N2, or inert gasses like Ar or mixtures, found to have a comparatively poor permeability for the wall.

As used herein the term "closed" may be understood to refer to pockets bound by walls having a negligible gas transmission rate (GTR). Generally a gas transmission in the order of 1 percent of the pocket volume per hour may be acceptable. Preferably the gas transmission is well below 1% per day.

In a preferred embodiment, e.g. as shown in FIG. 1B the resilient means is provided by the flexible wall comprising or essentially consisting of a shape recovering resilient composition C that is configured to recover the outwards protruding shape absent the external force.

Preferably, the flexible wall comprises or essentially consists of a thermoplastic elastomer composition. As will be explained in more detail with regard to FIGS. 11 and 12 the composition is preferably selected to have essentially elastomeric properties at a normal operating temperature of the system at about 25° C., preferably in a range 0-60° C. Preferably, the composition has thermoplastic properties at a thermoforming temperature above the normal operating temperature, e.g. above 70° C., preferably higher, e.g. at least 20° C. higher, most preferably above 100° C. such as 110 or 120° C. Selection of thermoplastic elastomer compositions within said ranges allows forming a system having sufficient structural integrity at normal operating conductions, while allowing manufacturing at reasonably achievable thermoforming temperatures.

Advantageously such materials were found suitable to form pockets having a leak rate or gas transmission well within the desired range.

Figure 3A:
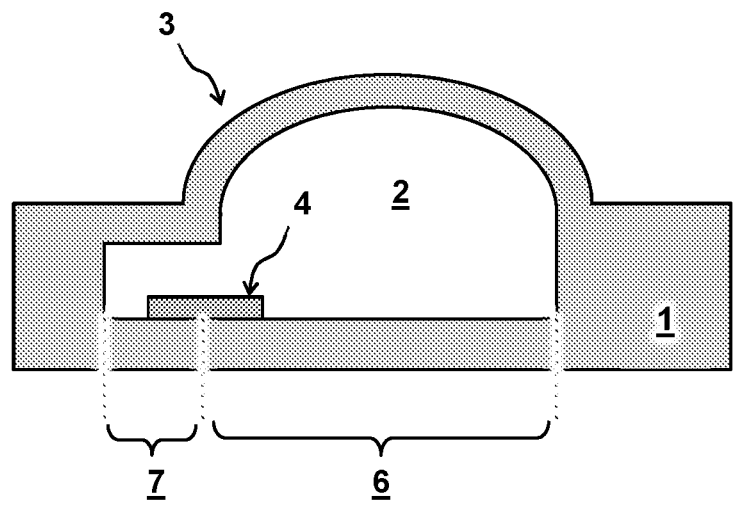
FIGS. 3A and 3B illustrate an embodiment of the system in cross-section side view and plan view.
Figure 3B:
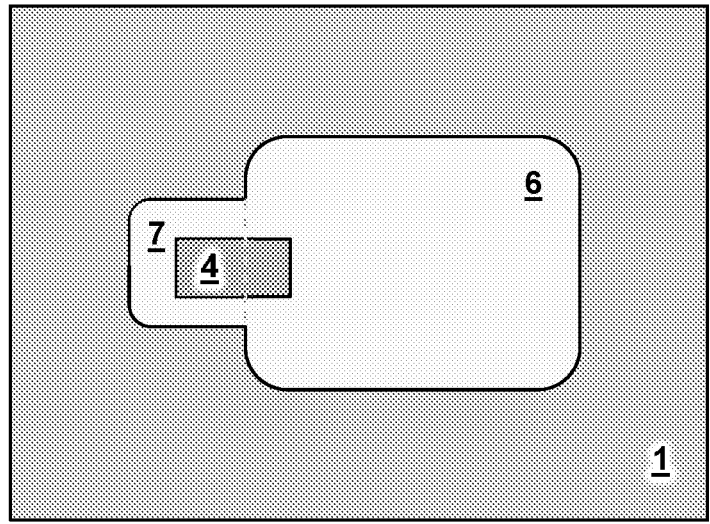

In particularly preferred embodiments the pocket 2 comprises a main volume and an adjacent volume. As illustrated by the embodiment shown in FIGS. 3A and 3B, the main volume 6 and adjacent volume 7 are in fluid connection. The adjacent volume 7 protrudes from the main volume 6 in a sideways direction within the substrate 1. The outwards protruding shape in the flexible wall is formed exclusively above the main volume 6. The MEMS device 4 is partly disposed in the adjacent volume. As such a person or object pressing onto the protruding shape will be less likely to sense the MEMS device, as compared to embodiments wherein the MEMS device is positioned directly under the protruding shape (see e.g. FIG. 1B-right).

Figure 4A:
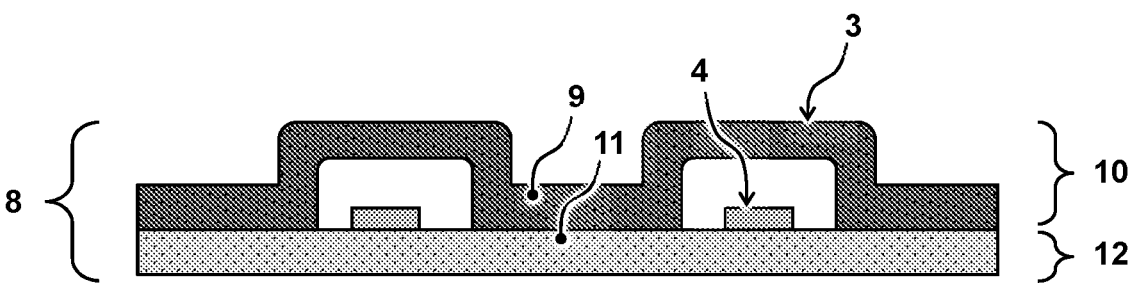
FIGS. 4A and 4B illustrate an embodiments of the system in cross-section side view.
Figure 4B:
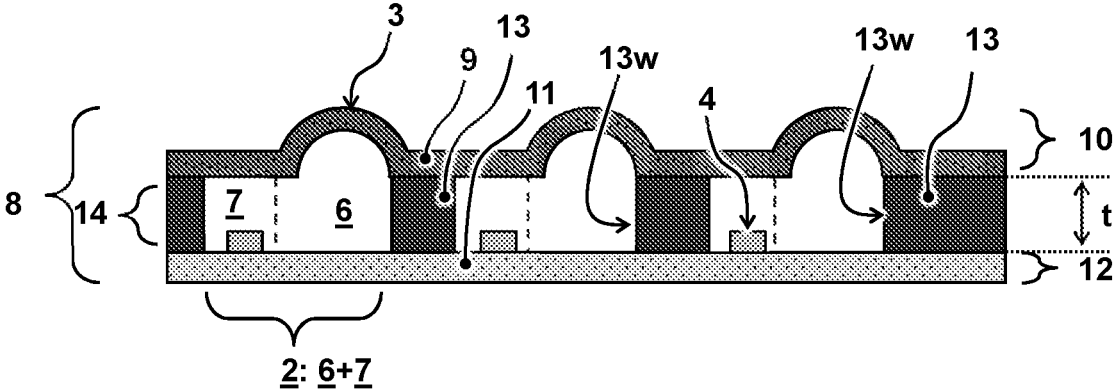

FIGS. 4A and 4B are illustrative of the aspect wherein the substrate comprises a stack 7 of two or more sheets 9,11,13.

The embodiment shown in FIG. 4A has a configuration wherein the stack comprises two sheets including a first sheet 9 forming a sensing layer 1 of the substrate that includes the flexible wall 3, and a second sheet 11 that forms a base layer 12 opposite the sensing layer. As shown the pockets 2 are formed by the two sheets between the opposing portions of the sensing layer and the base layer.

The embodiment shown in FIG. 4A has a configuration wherein the stack 8 includes a structured intermediate sheet 13, i.e. three layers. The intermediate sheet 13 forms a spacer structure 14 between the sensing layer 10 and the base layer 12 with an upstanding wall structure forming sidewalls 13w that laterally bound the pockets and separates pockets from adjacent ones. As shown, the spacer structure 14 is patterned so as to define a pocket 2 having a main volume 6 and an adjacent volume 7. The adjacent volume 7 extends from the main volume in a sideways direction between the sensing layer 10 and the base layer 12. The spacer structure 14 is patterned so that the protruding shape is exclusively positioned above the main volume. The MEMS devices 4 (see FIGS. 4A and B) see are disposed along the base layer 12, which simplifies manufacturing. In the embodiment shown in FIG. 4B the MEMS devices 4 are position inside the adjacent volume 7. Alternatively or in addition, MEMS devices can be disposed along the sidewalls 13w and or along the first sheet 9.

Figure 5A:
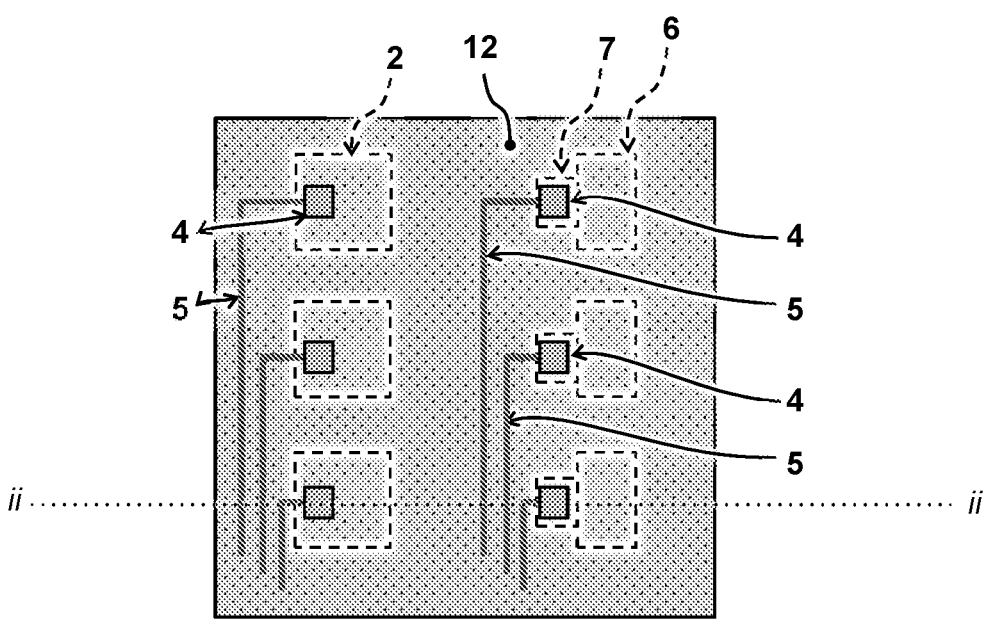
FIGS. 5A and 5B illustrate an embodiment of the system in plan view and in cross-section side view.
Figure 5B:
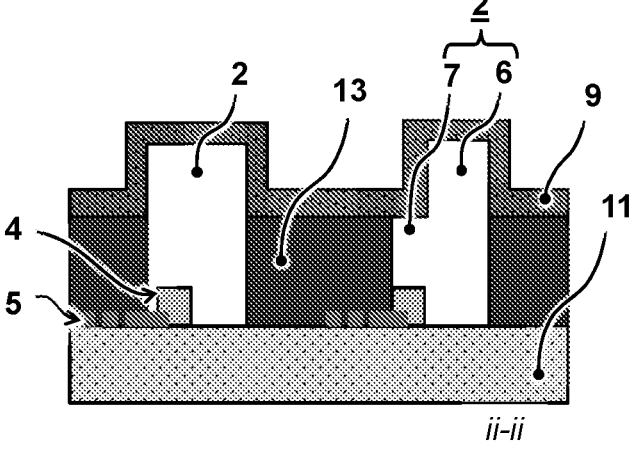

FIGS. 5A and 5B illustrates further aspects of the system according to the invention.

FIGS. 5A and 5B illustrates an embodiment in plan and cross section side view having a plurality of pockets 2 arranged in a 2×3 grid. Similar to the embodiment shown in FIG. 4B the pockets are bound by three sheets 9, 11,13, whereby the intermediate sheet 13 forms a spacer structure that laterally separates adjacent pockets. As shown, part of the pockets includes a main 6 and adjacent volume 7. The adjacent volume is formed in the sidewall of the pocket, whereby the adjacent volume is defined by a cutout extending the entire thickness of the intermediate sheet 13. Alternatively the adjacent volume can be defined by a partial cut-away or recess provided in the intermediate layer.

Provision of the spacer structure limits deformation of the pocket, in particular along its perimeter, formed by the sidewalls. This protects the MEMS from deformation, damage, and touch. Preferably, the sidewalls are configured to have a rigidity that exceeds a rigidity of the pocket, at least in a direction along the external force. In some embodiments, the spacer structure has a comparatively higher compressibility (lower rigidity) over a first trajectory for a first range and a lower compressibility over a second trajectory, e.g. a foam that has a high compressibility over a first trajectory that correlates to a fraction of pores, and a low compressibility or even essentially rigid behavior over a second trajectory that correlates to a dense or solid fraction of the material. As such the spacer may act as a backstop limiting compression of the pocket beyond a predetermined threshold.

The electrical circuitry for each of the MEMS devices is predominantly provided along a trajectory between adjacent ones of the pockets, preferably essentially covered by the spacer structure. Providing the wiring along a trajectory between pockets mitigates a risk of excessive flexing or stretching of the wiring. Covering the wiring by the space structure reduces deformations of the wiring due to bending and/or stretching of the substrate, in particular in presence of the external force.

As shown the sensing layer, the base layer, and/or the intermediate layer are each formed of an individual layer, preferably plastic film. Optionally the base layer can be a part or a portion of the sensing layer, e.g. by a fold.

Preferably the base substrate comprises or essentially consists of a second thermoplastic elastomer composition. Forming the base layer and sensing layer of thermoplastic elastomers allowing joining the layers at a temperature above a softening or glass transition temperature of at least one of the layers, e.g. by laminating. Preferably both comprise the same composition or at least a composition having a similar softening temperature as this would allow material from both layers to partake in the bonding process at a single bonding temperature.

Preferably, the spacer structure, when present, also comprises or essentially consists of a thermoplastic elastomer composition, i.e. a further thermoplastic elastomer composition having essentially elastomeric properties at normal operating temperature of the system and thermoplastic properties at a thermoforming temperature. Preferably, the spacer is formed of a composition having lower compressibility than the first and or second thermoplastic elastomer compositions.

More preferably the thermoplastic elastomer composition comprised in the spacer structure has a softening or glass transition temperature below a glass transition temperature of the thermoplastic elastomer composition comprised in the first and/or second flexible wall. This advantageously allows bonding the layers comprise in the stack without deforming the flexible walls, the protruding shape. Most preferably the softening temperature of the thermoplastic elastomer composition comprised in the spacer structure is at least 10° C. below a softening temperature of the lowest of the first and second sheets, while still being sufficiently distant, preferably by at least 20° C. above the normal operating temperature range of the system. For example, the softening or glass transition temperature of the thermoplastic elastomer composition comprised in the spacer structure can be in a range above 50° C., preferably higher, e.g. above 60° C. or above 80° C., as this allows operating the system at higher temperatures without affecting the bond between the layers. Preferably, the Tg is ≥90° C. or higher, e.g ≥100° C., depending on a Tg of the remaining layers.

Preferably, the walls bounding the pockets are essentially closed. However, some permeability can be tolerated, e.g. via interstice spaces within the polymer compositions comprised in the bounding walls Generally, the leak rate is below about part per hundred (1%) per hour. Preferably lower, e.g. below 1% per day. The lower the leak rate the longer the sensor cane be operated under static load. Typically the leak rate is between leak rate of 1% per hour and 1 part per thousand (1% %) per day. Generally, the walls bounding the pocket have an air transmission rate between an upper limit R2 of about 240 cm³/m²/24 h/atm and a lower limit R1 close or equal to about 0 cm³/m²/24 h/atm, or at least ≤10 cm³/m²/24 h, at 0° C. as determined by ISO2556:1974.

Preferably the MEMS sensor is what is a MEMS barometric sensor. MEMS barometric sensors are generally known as high accuracy pressure sensors and a commercially available from a number of suppliers. As an example a MS5637-02BA03 from TE Connectivity Ltd. may be used. To process the data or combine it in a tag an MSP430 microcontroller or equivalent can be used or alternatively a RF430FRL152H combined NFC microcontroller IC with energy harvesting can be used.

A barometric pressure sensor generally comprises a closed sensing volume bound along at least one end by a flexible membrane coupled to with readout electronics. Advantageously such sensors are highly energy efficient.

Generally requiring less than 0.6 µA to operate. By integrating it in a patch a UHF based wireless and batteryless systems, such as breathing and heart rate sensors, can be made that can be read-out remotely, even at a distance up to 10 meters. To do so one can use a combination of a Impinj Monza X-8K, a P2110 Power harvester and a MSP430 microcontroller or equivalent.

FIGS. 6A to 6C illustrate embodiments of a MEMs device that can be comprised in the system. Such sensor generally comprise a enclosed volume 44 that is bound between a flexible membrane 43 and a base substrate 41. The membrane is typically a thinned down portion of a top layer 42 usually of a semiconducting material like silicon made using conventional microfabrication techniques such as back-etching. The top layer is bonded to the base to form a closed cell. Sensing electronics 46,47,48, generally based on capacitive (FIG. 6A) or resistive principles (FIG. 6B), yields an electric signal S with is proportional to a pressure difference between the pressure inside the enclosed volume and an external pressure. Read-out is typically performed by an integrated controller 60.

Preferably, the flexible membrane 43 bounding a closed sensing volume 44 of the MEMS device has maximum air transmission rate R3 that is smaller than R1. Most preferably R3 is at least ten times smaller than R1. This minimizes potential drift of the MEMS device. Most preferably the flexible membrane is essentially closed for relevant timescales during normal operating conditions.

In preferred embodiments, e.g. as shown in FIG. 6C, the MEMS device 4 is enclosed in a rigid housing 50. The enclosure protects the MEMS device, in particular the delicate membrane, from direct contact by external objects. The enclosure has at least one aperture 51 that provides a fluid connection to the flexible membrane of the MEMS device. Typically the aperture is provided in a top face, facing the membrane, of the enclosure, e.g. as shown. However it will be understood that the aperture can be provided in top, side, bottom walls or any combination thereof. in any case the MEMS device will be positioned so that there is a fluid connection between the flexible membrane and the pocket 2 of the system.

In a preferred embodiment, e.g. as shown in FIG. 6C, the MEMS device comprises an integrated temperature sensor 52. The output of which can be used to measure temporal temperature variations over spatial temperature variations for systems comprising a plurality of MEMS devices.

In some devices, e.g, wherein the pickets if filled with a liquid or a gel the, the MEMS device can be pneumatic pressure sensor.

Figure 7A:
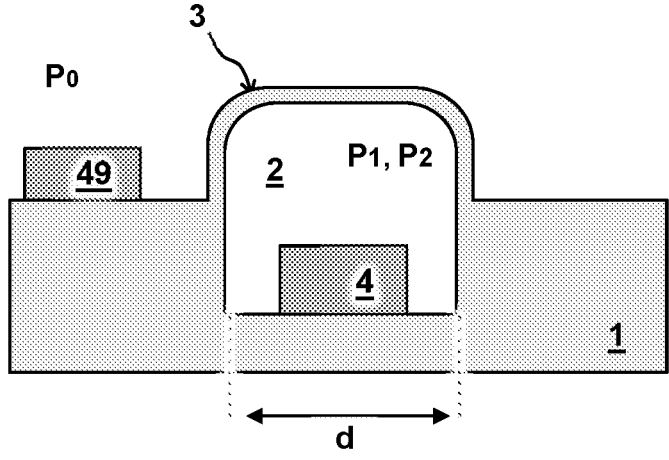
FIGS. 7A and 7B illustrate embodiments of the system in cross-section side view.

In other or further embodiments, e.g. as shown in FIG. 7A the system comprises a reference pressure sensor 49. The reference sensor can be a further one of the MEMS device 4, e.g. of the same or a similar type. The reference sensor 49 can advantageously be used to correct on output of the MEMS device 4 in response to external load conditions for variations in ambient pressure. This can be of particular relevance when the sensor is used to measure comparatively small forces or pressures (e.g. in a range below 1 or 10 grams) which would lead to pressure variations P1,P2, inside the pocket that are of in a range of a few Pascal (e.g. from 1 Pa or 10 Pa) up to a couple hundreds of pascals (e.g. up to 500 or 1000 Pa).

Figure 7B:
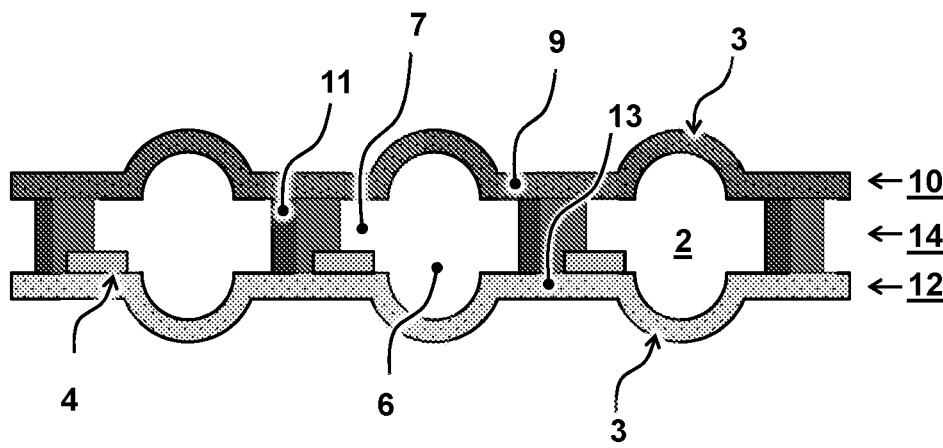

In some embodiments, e.g. as shown in FIG. 7B the base layer 12 is provided with an outwards protruding shape 3 configured to flex inwards into the pocket 2 for increasing the pressure inside the pocket in the presence of the external force and provided with a resilient means configured to recover the outwards protruding shape absent the external force, forming a second sensing layer opposite the first.

Generally, the pockets have a cross section (d) dimension larger than 1 cm, e.g. about 2 cm, or larger, e.g. in a range between 1 and 5 cm or 1-10 cm. Larger pockets advantageously offer improved sensing over larger areas with comparatively limited number of pockets. In contrast, known barometric pressure sensors, such as the MEMS devices comprised in the system according to the present disclosure, generally measure only very locally.

The protruding shape typically has the height in excess of 0.5 mm, preferably in excess of 1 or even ≥2 mm, e.g. in a range between 1 and 3 mm or in a range between 2 and 5 mm. The higher the protrusion the larger the potential inward displacement of the flexible wall and the less likely a user will sense or feel the opposing bound to the pocket or present of the MEMS devices. Typically the height provided by the protruding shape of the flexible wall contributes at least 20% of the total height of the pocket, preferably more, e.g. at least 40%, more preferably up to 50%, e.g. between 20 and 50% or between 40 and 50%. In this way the pockets cannot be fully compressed as the flexible wall does not flex inwardly down to an opposing wall. As such a user will be less likely to touch/feel the opposing wall of the pocket and/or elements (e.g. MEMS device) provided along the base layer.

The thickness (t) of the intermediate sheet is generally in a range between 0.1 mm and 0.5 cm, preferably between 0.2 mm and 3 mm, most preferably between 0.5 and 2 mm, e.g. about 1 mm. The higher the space structure the more room to accommodate inward flexing of the flexible wall 3 and the larger the range of potential pressure variation inside the pocket in response to an external stimulus.

The aspect ratio, defined as a total height of the pocket, as the sum of the height provided by of the upstanding wall structure and the height provided by the protruding shape of the flexible wall 3 divided by a distance between opposing upstanding walls is generally in a range between 0.05 and 1, typically between 0.1 and about 1.

Thermoplastic elastomer compositions were found particularly suitable of sustaining pockets with a relevant dimensioning.

Figure 8A:
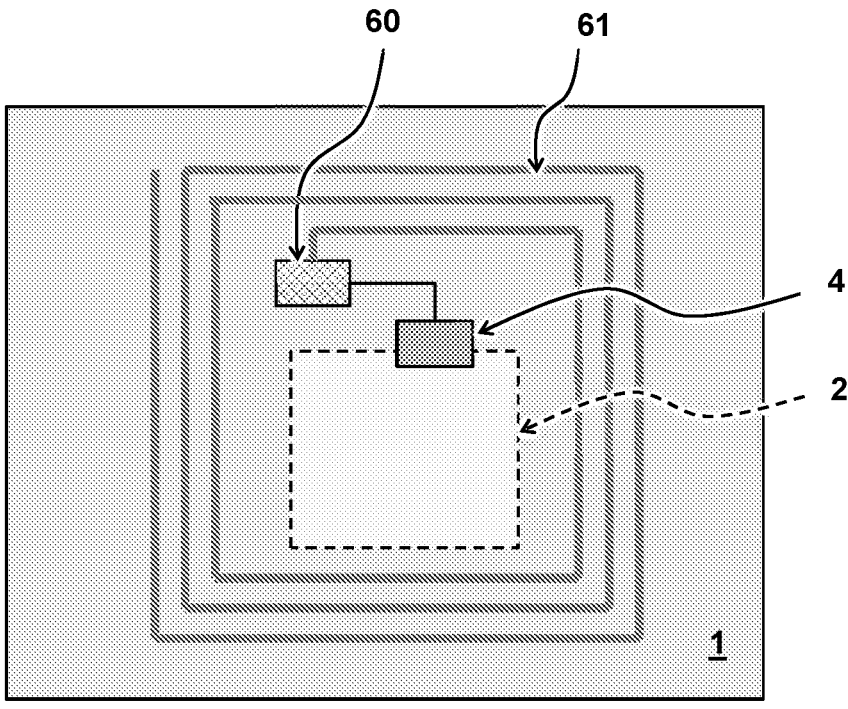
FIGS. 8A and 8B illustrate embodiments of the system in plan view and in cross-section side view.

In some preferred embodiments, e.g. as illustrated in FIG. 8A, the system includes electronics 60,61 for remote, wireless, communication with an external electronic device. This advantageously remote readout of the set of MEMS devices. The electronics can be provided as a wireless tag, which typically contains a microcontroller, a power supply such as a battery, and radio IC. The tag advantageously enables that the data of sensor may be streamed or logged on or from the tag to another device, said phone, tablet or dedicated portable device using a defined wireless protocol such as Bluetooth, NFC or WIFI. In another aspect the sensor tag may stream the information directly to a local or remote server, for example using protocols such as WIFI, Lora, Sigfox or Zigbee.

Advantageously, the system can further include an energy harvester to power the device, for example a receiver for inductive powering of the set of MEMS devices. The harvester can be provided for example as an RFID tag or NFC tag. Wireless communication or remote powering, preferably both, improves flexibility and freedom of movement during operation of the system. Advantageously the system according to the invention may be particularly suitable for remote powering at least in part due to the particular low power demand of the MEMS devices comprised in the system. Advantageously, the electronics, tags including wiring, coils, and/or antennas 61 comprised therein, may be provided onto the base layer 1 using convenient manufacturing methods such additive manufacturing methods as printing including but not limited to LIFT and (screen) printing. The electronics can advantageously be dimensioned and/or positioned so as to minimize impact on the overall dimension of the system. For example, the electronics can be positioned at least partially surrounding, besides, between and/or even under pockets 2. Alternatively the system may include wired readout electronics and/or a non-transient data storage medium. Alternatively or in addition, the system may include contact points, e.g. bond pads, clips, and/or buttons for connecting to an external readout and/or power source.

Figure 8B:
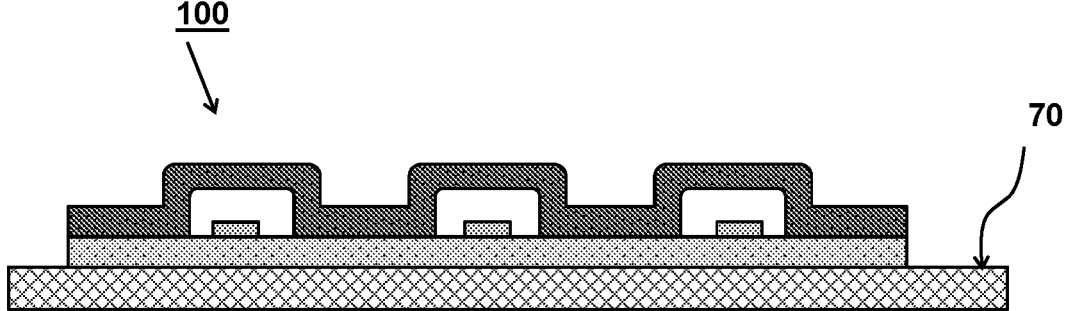

In some preferred embodiments, e.g. as shown in FIG. 8B, the system 100 is integrated with or adhered along a flexible carrier (70), typically a textile layer. Integrating or adhering the system along a flexible carrier allows conforming the system to an outer perimeter of a body part or user product. For example, ample in the of rom a textile product, garment or cover for a bedding or seating product.

Figure 9A:
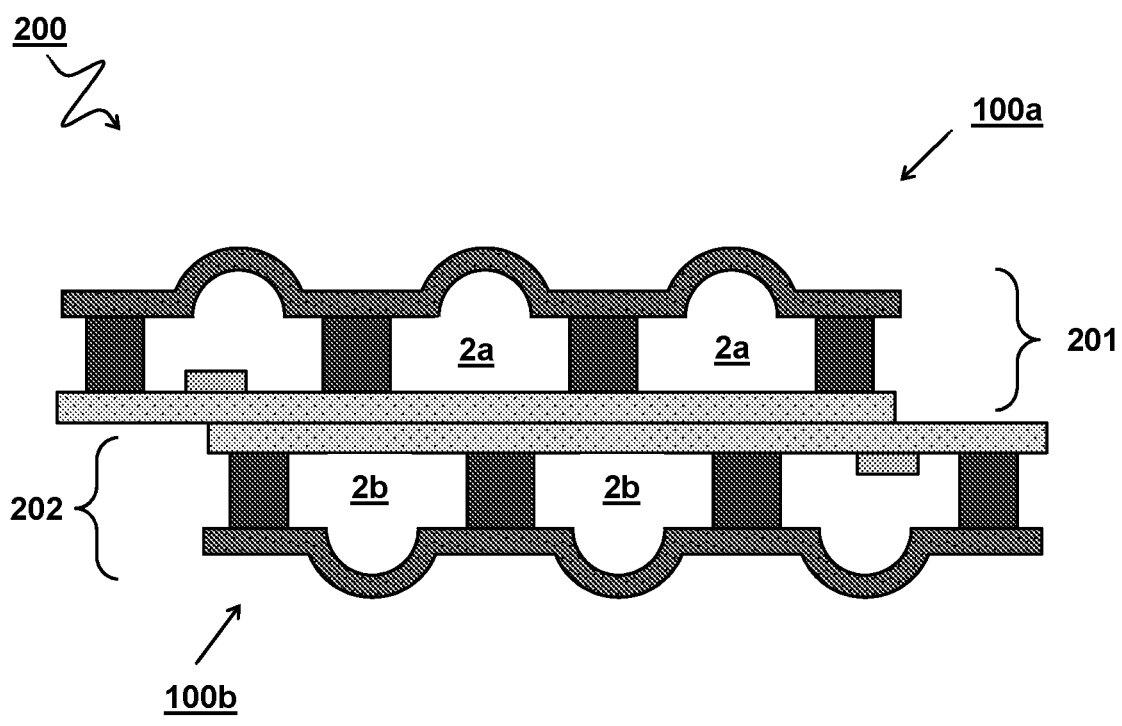
FIGS. 9A and 9B illustrate embodiments of an assembly and a garment comprising the system.

In yet further embodiments, e.g. as shown in FIG. 9A, there is proved an assembly 200 that comprising a layered stack 201,202 comprising first 100a and second ones 100b of the systems as disclosed herein. In some embodiments, e.g. as shown, the systems are stacked back to back which allows sensing of forces from opposing directions. In some embodiments, the system comprises systems that are stacked face to face, e.g. in two, three, four or even more layers. Stacking a plurality of systems distributes forces experiment within one layer and increases overall operational range. In addition the stacking reduces transduction localized forces (e.g. point forces) down to an underlying object or body part. In some preferred embodiments, layers 201, 212, are arranged so that the pockets 2a comprised in a first layer 201 are shifted laterally with respect to the pockets 2b comprised in a second layer 202 of the stack. laterally shifting the pockets advantageously improves accuracy of a determined pressure or force distribution for a given pocket size.

Figure 9B:
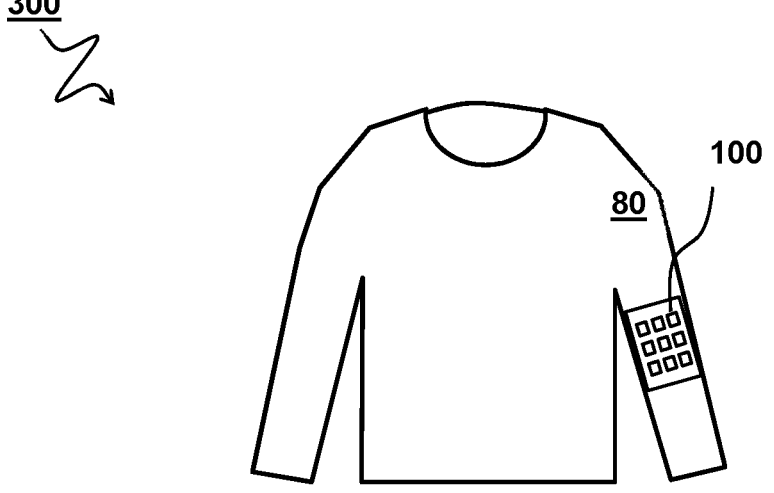

According to some aspects, e.g. as shown in FIG. 9B, the disclosure concerns as clothing product 30 comprising one or more of the systems as disclosed herein.

According to further or other aspects the disclosure concerns a or personal monitoring product or a diagnostic product 400, 401, 402 comprising the system 100 as disclosed herein. As disclosed herein said product band be used to measure a condition of the person, including but not limited to a breathing rate and a heart rate. Inventors found that the system can be used to measure vistal signs including respiration and heart rate of an infant or neonate.

In some embodiments, e.g. as shown in FIG. 10A, the product 401 is or is comprised in a band 90 for wearing around a chest of a person 1000. In some embodiments, e.g. as shown in FIG. 10B, the product 401 is a compression bandage 91 comprising the system 100 as disclosed herein. Alternatively the system may be provided as an inlay for used with a conventional compression bandage. Said bandage 91 or combination of inlay and can be used to advantage to optimize bandage pressure, e.g. for persons unable to communicate, to monitor pressure evolution as function of time, e.g. to detect/monitor a swelling condition of a body part.

Figure 10C:
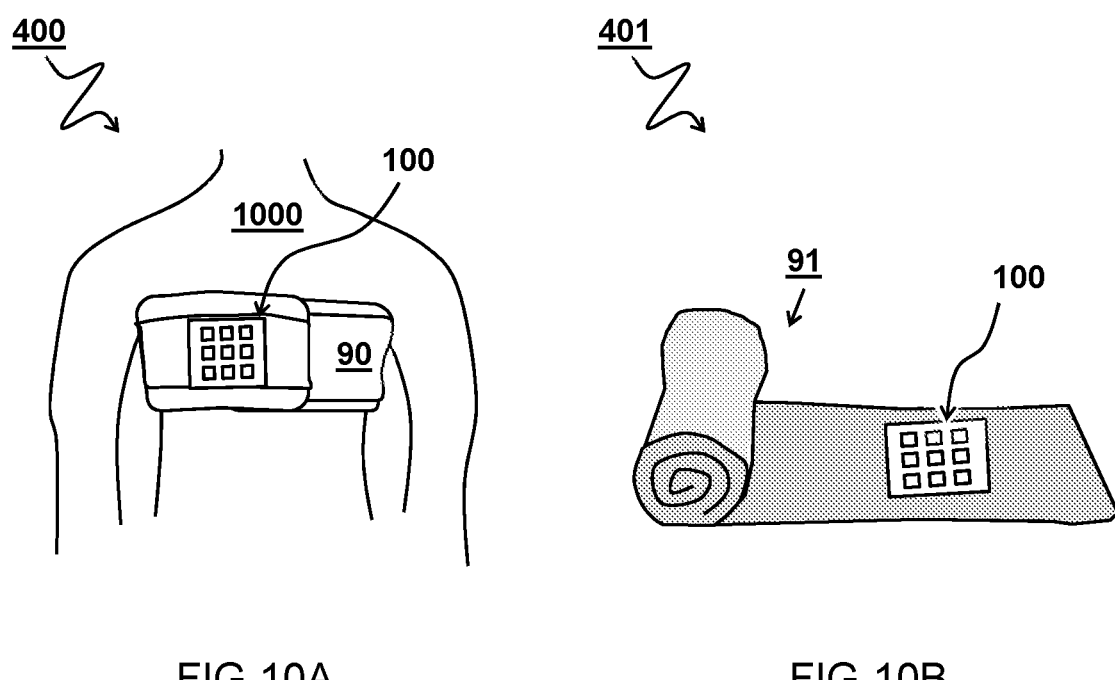
Figure 10C:
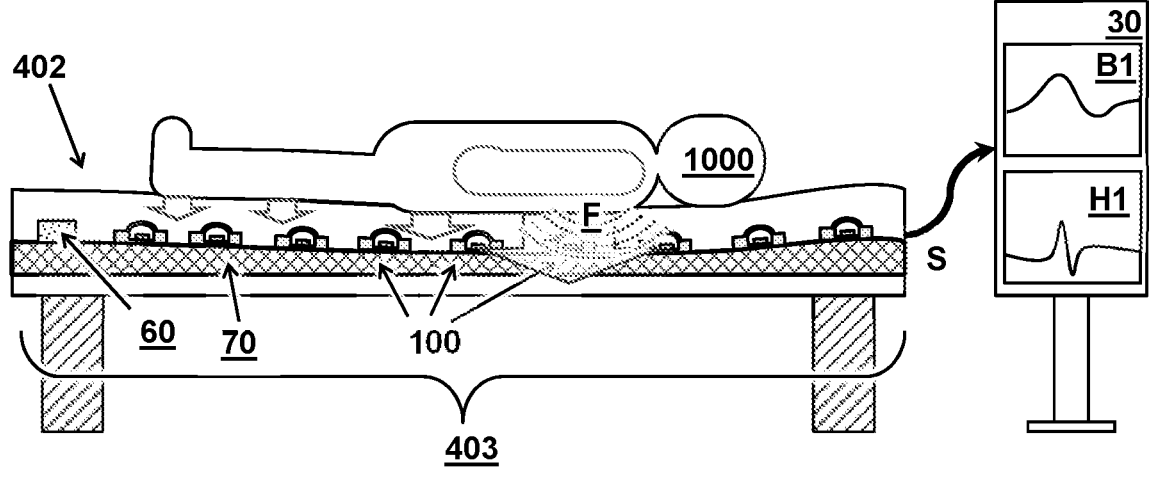

In some embodiments the system is comprised in a bedding product 403. FIG. 10C schematically illustrates a diagnostic product 402 comprising system 100 as disclosed herein in in the form of a bed 403. The product 402 comprises a plurality of the system 100 distributed to measure force F between person and bed. The product 402 can be used to determine pressure distribution as well as a presence of pressure points and their evolution over time. As such the product can be used in the treatment of prevention of pressure ulcers also known as pressure sores or bed sores, which are generally considered to relate to localized damage to the skin and/or underlying tissue that usually occur over a bony prominence as a result of usually long-term pressure, or pressure in combination with shear or friction. Alternatively, or in addition, the product can be used to monitor a breathing rate and or heater rate of the person while lying on the bed, for example using a display 30 configure to display a breathing rate B1 and heart rate H1 using the output signal S of one or more of the systems 100.

Figure 15:
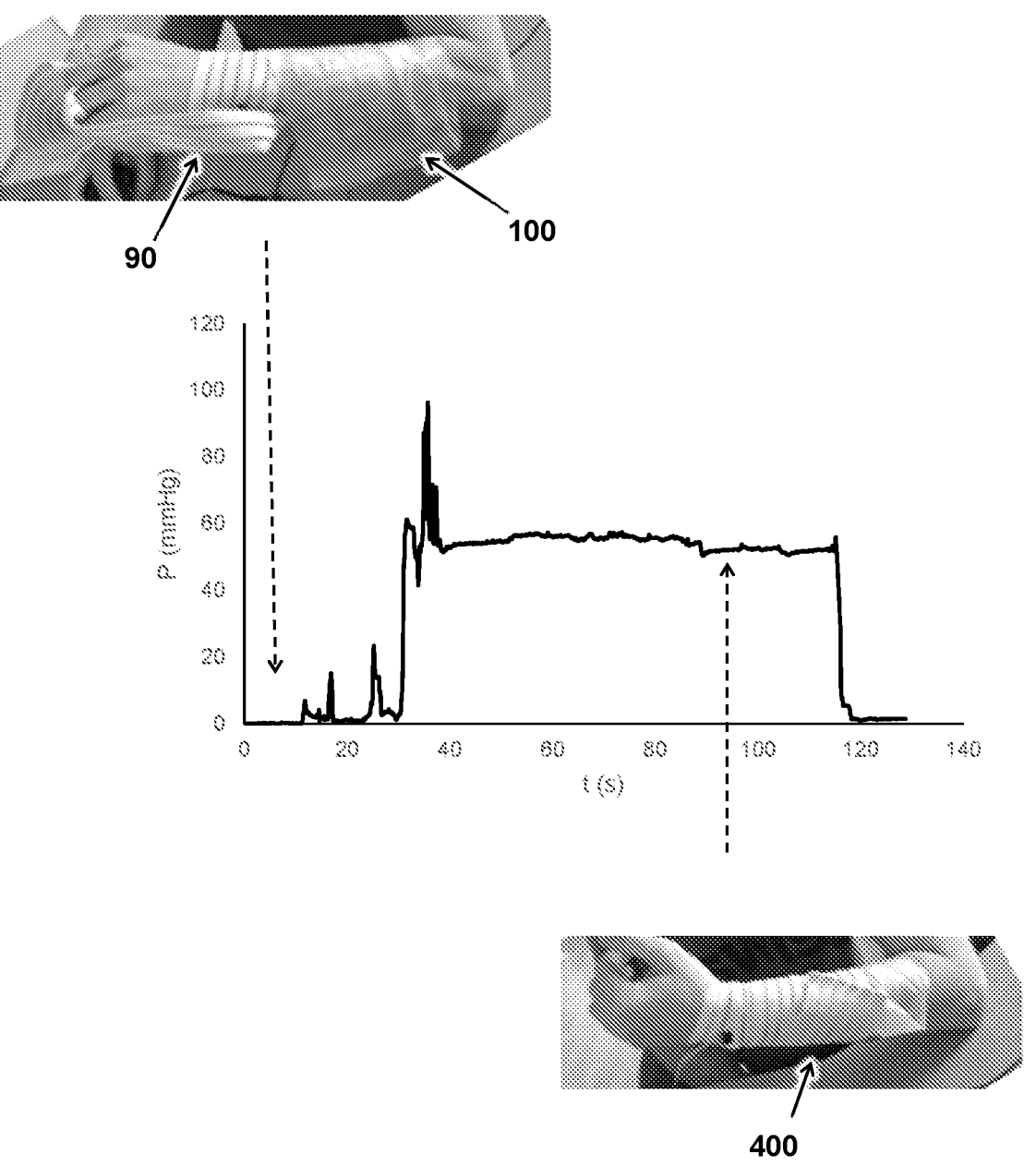

It will be appreciated that in alternative embodiments the product can be embodied as underlayment, e.g. for use with any of de applications described in relation to FIGS. 9B, 10A, 10B, and 10C, e.g. as shown in FIG. 15 showing an system comprising a plurality of pockets arranged in an array applied as underlayment between the skin of a subject and a compression bandage.

Aspects relating to the method 500 of manufacturing the system 100 as disclosed herein will now be described with reference to FIGS. 11 and 12.

In one embodiment, the method comprises providing a set of MEMS devices 4 inside a respective one or more closed pockets formed by a substrate, each pocket having at least one flexible wall deforming as function of an external force applied to the flexible wall, each MEMS device configured to cause variation of an electric signal as function of a pressure inside the respective pocket; wherein the flexible wall is provided with an outwards protruding shape configured to flex inwards into the pocket for increasing the pressure inside the pocket in presence of the external force and provided with a resilient means configured to recover the outwards protruding shape absent the external force. Preferably, the resilient means is provided by the flexible wall comprising a shape recovering resilient composition configured to recover the outwards protruding shape absent the external force.

Figure 11A:
FIGS. 11A, 11B and 12 illustrate a method of manufacturing the system.
Figure 11A:
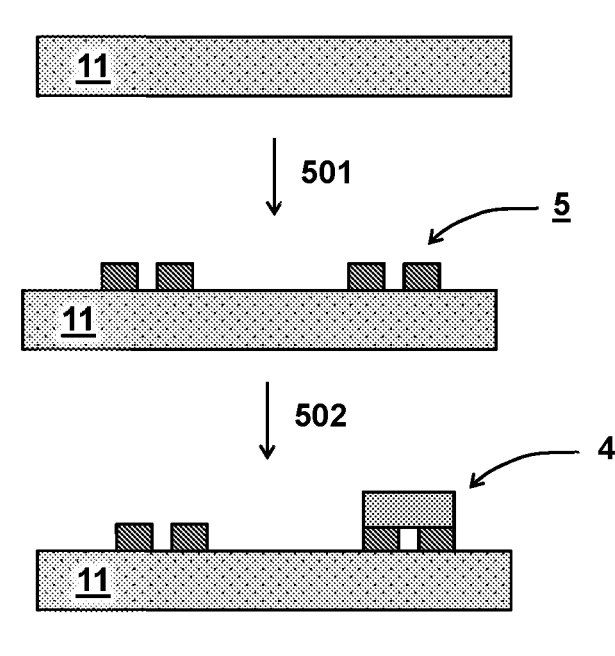
Figure 11B:
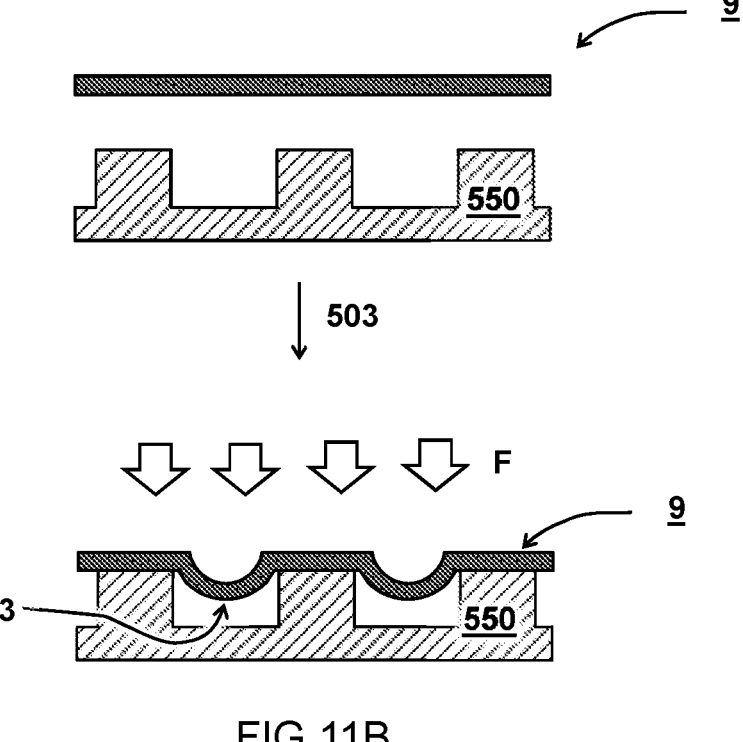

In some embodiments, e.g. as shown in FIG. 11A the method includes depositing 501 wiring 5 along a face of a base layer followed by positioning MEMS devices 4 onto the writing. The wiring and/or MEMS devices may be provided by any suitable deposition method. Preferably, the components are positioned using additive manufacturing processes including but not limited to (screen) printing, flexoprinting, LIFT and pick and place methods.

In embodiments wherein the resilient means is provided by the flexible wall the flexible wall is can be formed in a step 503 comprising thermoforming 503 portions of a sensing layer 9 at positions in correspondence with the respective pockets using a thermo press 550 applying appropriate force F while the film is heated to a temperature above a thermoforming temperature.

In some embodiments, forming the substrate comprises laminating the sheets to respective opposing sheets along outer perimeters of the respective pockets.

In some embodiments, the MEMS devices and electronic wiring for interfacing with each of the MEMS devices are disposed along the base layer.

In some embodiments, disposing the electronic wiring for interfacing with each of the MEMS comprises printing of an ink comprising electrically conductive filler material and an elastomer matric material or precursor thereto.

In some embodiment formed sheets 9,11 are stacked together so as to form a system 100 as described in relation to FIG. 4A (without spacer structure 14), whereby the sheet 11 including the MEMs and wiring forms the base layer 12 of the stack 8 and the sheet 9 forms the sensing layer 10.

In preferred embodiments, wherein the system 100 includes a spacer structure 14, e.g. as described in relation shown in FIGS. 4B, 5B and 7B, the method includes a step 505 of providing a patterned intermediate sheet 13 to form a spacer structure between the sensing layer and the base layer with an upstanding wall structure forming sidewalls that laterally bound the pockets and separates pockets from adjacent ones.

Said intermediate sheet may be provided by additive manufacturing methods such a sprinting. For example by directly depositing a suitable composition directly a onto the first sheet 9 and/or the second sheet. In a preferred embodiment, e.g. as shown in FIG. 12, the spacer structure is provided by patterning 505 positions of a virgin sheet 13*a* to include respective apertures 6*a*, 7*a* at positions in accordance with the main volume 6 and adjacent volume 7 of the pocket.

Subsequent to forming the intermediate sheet 13, sheets 9,13, and 11 are stacked and bonded, laminated, in a membrane press 551 fusing the bubble structure 9 in the frame 551 to the conductive track support using with the intermediate layer as an adhesive therebetween. After lamination the frame 550 and any liners to avoid adhesion of layers to the frame are removed. In case the system 100 is to be attached to a carrier, e.g. a textile the liner is removed from the bottom substrate, then the pressure sensor is laminated onto carrier with the frame in place.

In a preferred embodiment, the sheets 9,11, and/or 13, include a layer coating having a thermoforming temperature below a softening temperature below a glass transition temperature of the thermoplastic elastomer composition comprised in the first and/or second flexible wall. This allows laminating the stack at a temperature without substantially deforming the protruding shape. Alternatively, or in addition, the intermediate sheet 13 can comprise or consist of a composition having a thermoforming temperature below a softening temperature below a glass transition temperature of the thermoplastic elastomer composition comprised in the first and/or second flexible wall.

In a strongly preferred embodiment, the method comprises printing 501 electroconductive circuitry onto a sheet 11 comprising a thermoplastic elastomeric composition, preferably a elastomeric sheet comprising a thermoplastic top layer or coating. After providing circuitry a MEMS device is positioned and connected to the wiring, e.g. using pick and place methods.

Simultaneously, precedingly or thereafter the method comprises thermoforming 503 regions of a sheet 9, comprising a thermoplastic elastomeric composition, to form protrusions, e.g. domes. Sheets 9,11 may be comprised of the same or a similar composition.

After forming both sheets the sheets are positioned over each other where by the space provided the protrusion is positioned so that it is in fluid connection to the MEMS device. After positioning the sheets are laminated to each, forming a closed pocket between the sheets, e.g. as shown in FIG. 4A. As described in relation to FIGS. 1A and B sheet 11 forms a flexible wall 3 with an outwards protruding shape that is configured to flex inwards into the pocket for increasing the pressure inside the pocket in presence of the external force.

Figure 12:
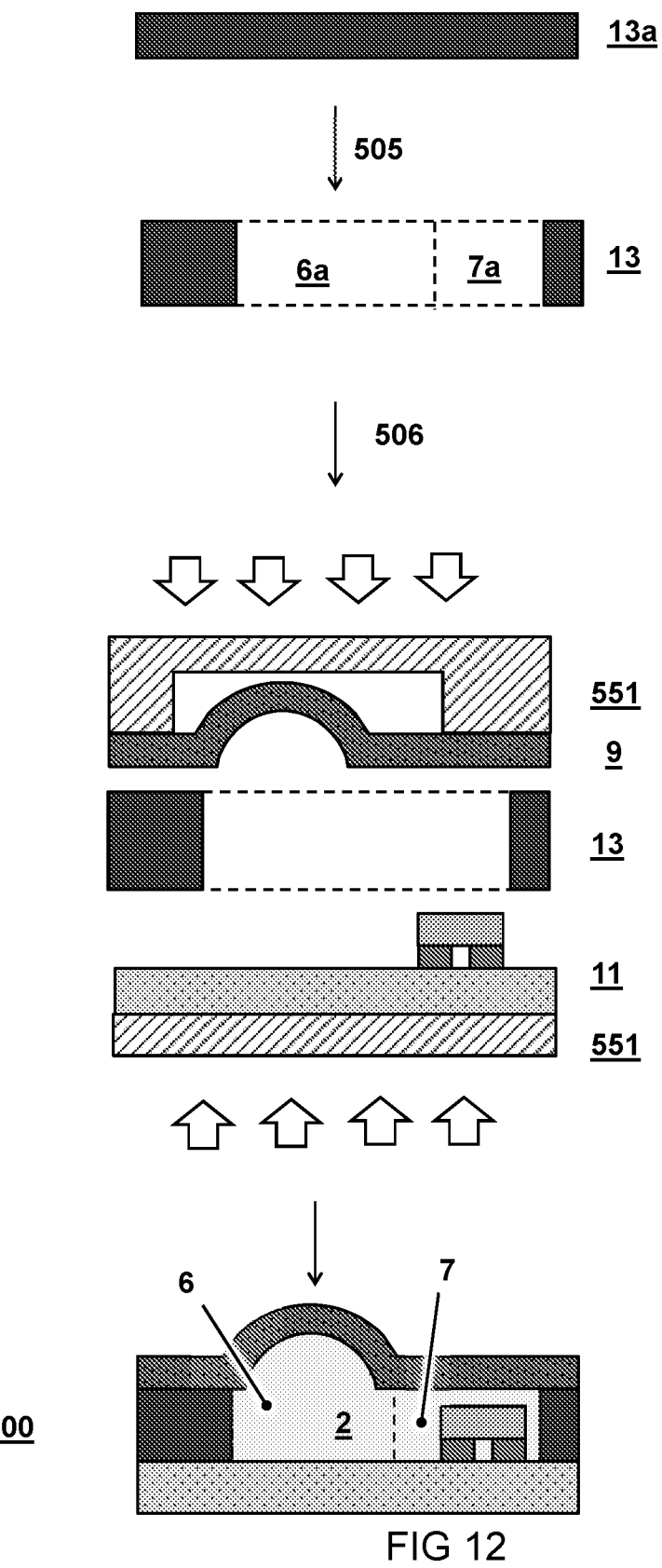

In a most preferred embodiment, e.g. as shown in FIG. 12, an intermediate sheet 13 is laminated between the first sheet 9 and the second sheet 11. The intermediate sheet 13 is patterned to include apertures 6a, 7a at positions in accordance with a main volume 6 and an adjacent volume 7 of the closed pocket 2 to be formed upon lamination. The protruding shape is exclusively above the main volume and the MEMS device is at least in part positioned in the adjacent volume. a patterned intermediate sheet 13 is positioned in between the sheet with the thermoformed protrusions 9 and the sheet bearing the MEMS devices. The intermediate sheet 13 has been pretreated by laser cutting to include a first cut out 6a and a second cutout 7a in fluid connection therewith that respectively corresponds to the main 6 and adjacent volume 7 of the pocket 2 to be formed. As disclosed herein the intermediate sheet forms a spacer structure 14 between the sensing layer and the base layer of the device with an upstanding wall structure forming sidewalls 14w that laterally bound the pockets and that separates pockets from adjacent ones.

It will be understood that the system 100 can be manufactured in a number of different ways. While laminating is can be preferred for reasons of scalability alternative ways, such as gluing, can be used. Similarly alternative ways can be used to for the wiring, spacer structure and/or sensing layer 10 including the flexible wall 3 with the protruding shape. including but not limited to additive manufacturing methods and/or molding.

FIGS. 13 to 15 show illustrative experimental results of systems manufacture according to the procedure as descried above.

Figure 13A:
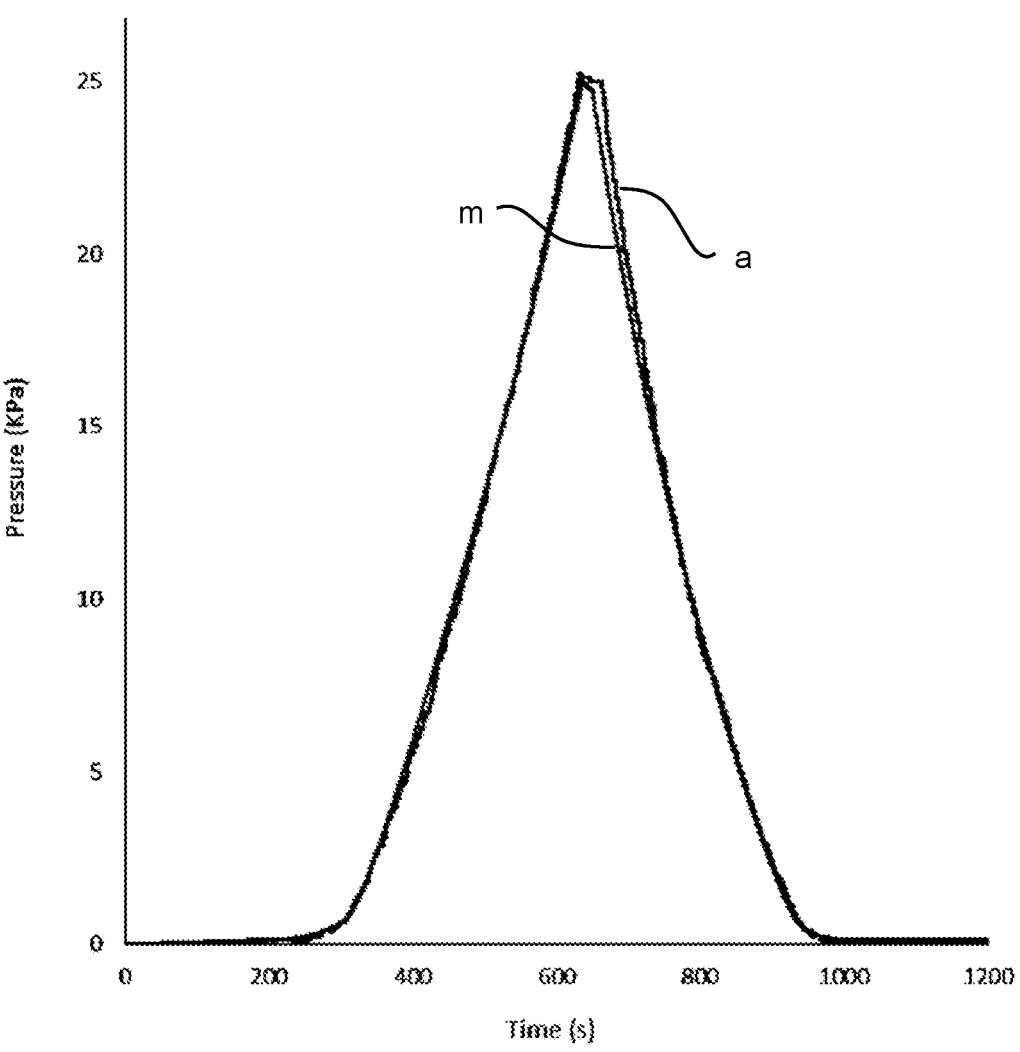
FIGS. 13 to 15 show illustrative experimental results.
Figure 13B:
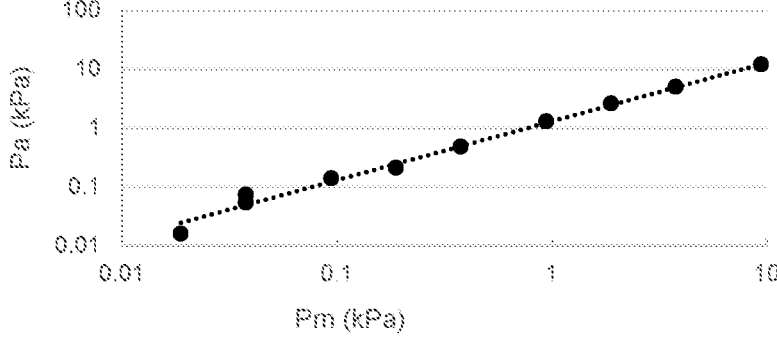

FIGS. 13A and 13B illustrate the performance of a system 100 comprising a single pocket enclosing a single MEMS device. As can be seen there is an excellent relation between a test pressure (a, pa) applied onto the flexible wall 3 and the corresponding measured response (m, pm) of the MEMS device. Over the applied range no significant issued were found with regard to hysteresis, drift or other artefacts such as leakage.

As shown in the corresponding plot in FIG. 13B there is an accurate and linear relation 20 about Pa up to the tested maximum of to 10 kPa. The pockets were found to be scale up to 100 kPa. While the baseline pressure may vary due to variations in ambient pressure the pressure differences, the change, is an accurate measure of the applied force.

Figure 14A:
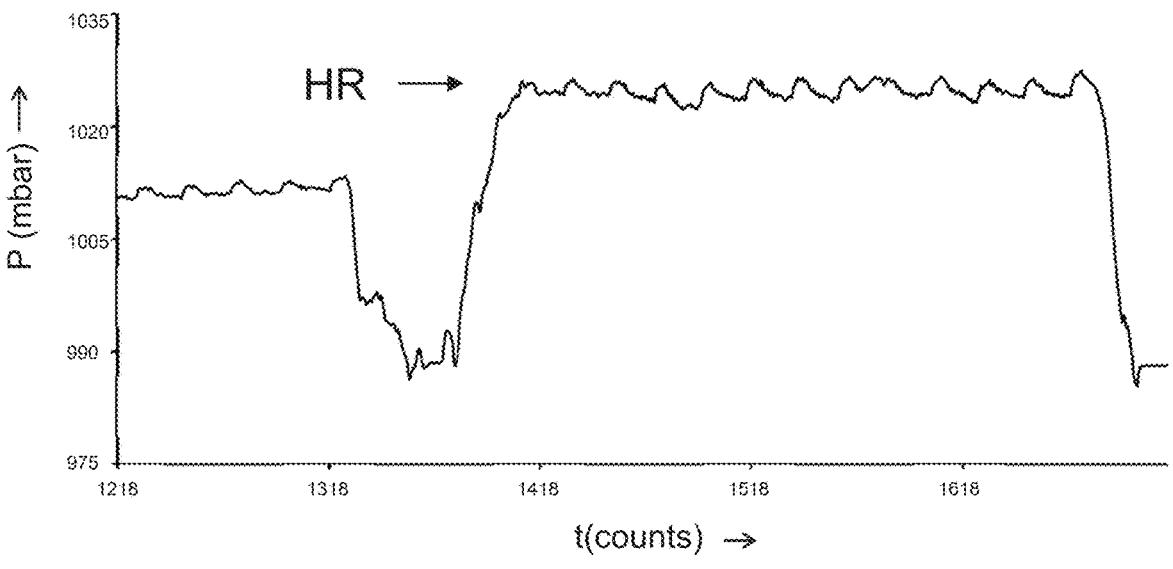
Figure 14B:
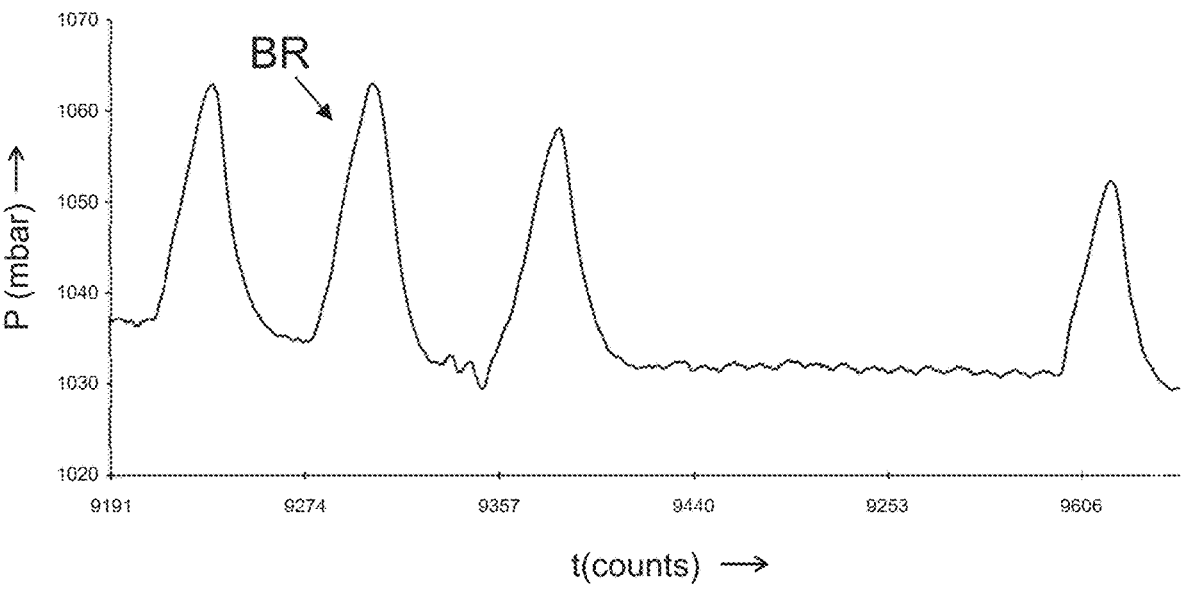

FIGS. 14A and 14B illustrate how the system can be used to determine vital system of a person. In the test a system according to the invention was brought with a person at a position near the sternum. As shown in the plot in FIG. 14A the system as able to record pressure variations in the order of 2 mbar that correspond to the subjects heart rate HR. As shown in FIG. 14B the same system could be used to a response indicative of a breathing event (BR).

The plot in FIG. 15 illustrates that the system 100 can be used an inlay under a compression bandage 90 to measure a pressure exerted by said bandage onto a person's fore-arm. At time 0-10 s (see top photo) the system 100 was not yet covered by the bandage. At time 10-40 effects relating to the application of the bandage are shown. At time 40-115 the bandage is applied to the fore-arm an applies a pressure of about 50 mmHg. Variations are believed to related to variations in tensioning of the subjects muscles. At t 115 the bandage is released.

For the purpose of clarity and a concise description, features are described herein as part of the same or separate embodiments, however, it will be appreciated that the scope of the invention may include embodiments having combinations of all or some of the features described. The various elements of the embodiments as discussed and shown offer certain advantages, such as conformability and accuracy in combination with an ability to function without external tubing or pressuring tools. Of course, it is to be appreciated that any one of the above embodiments or processes may be combined with one or more other embodiments or processes to provide even further improvements in finding and matching designs and advantages.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context. The present disclosure further relates to embodiments as specified by the following listed clauses.

Clause 1. A system (100) for measuring external force (F), the system comprising: a substrate (1) forming a set of closed pockets, each pocket (2) having at least a flexible wall (3) deforming as function of the external force; a set of MEMS devices (4), each configured to cause variation of an electric signal(S) as function of a pressure (P) inside a respective pocket; wherein the flexible wall is provided with an outwards protruding shape configured to flex inwards into the pocket for increasing the pressure inside the pocket in presence of the external force and provided with a resilient means configured to recover the outwards protruding shape absent the external force.

Clause 2. The system according to clause 1, wherein the resilient means is provided by the flexible wall comprising a shape recovering resilient composition (C) configured to recover the outwards protruding shape absent the external force.

Clause 3. The system according to clause 1 or 2, wherein the flexible wall comprises a thermoplastic elastomer composition.

Clause 4. The system according to any of the preceding clauses, wherein the pocket (2) comprises a main volume (6) in fluid connection to an adjacent volume (7) protruding sideways from the main volume, wherein the outwards protruding shape in the flexible wall is formed exclusively above the main volume and the MEMS device is at least in part, preferably completely, disposed in the adjacent volume.

Clause 5. The system according to any of the preceding clauses, wherein the substrate (1) comprises a stack (8) of two or more sheets including a first sheet (9) forming a sensing layer (10) of the substrate that includes the flexible wall (3), and a second sheet (11) forming a base layer (12) opposite the sensing layer, whereby the pockets (2) are formed between the sensing layer and the base layer, wherein the stack (8) includes a structured intermediate sheet (13) forming a spacer structure (14) between the sensing layer and the base layer with an upstanding wall structure forming sidewalls (14w) that laterally bound the pockets and separates pockets from adjacent ones.

Clause 6. The system according to any of the preceding clauses 4-5, wherein the adjacent volume is formed in the sidewall of the pocket.

Clause 7. The system according to any of the preceding clauses, wherein the system comprises a reference pressure sensor (49) positioned outside the closed pocket.

Clause 8. The system according to any of the preceding clauses, wherein the system is configured to receive a reference pressure from an external device, preferably a mobile device, upon pairing with the external device.

Clause 9. The system according to any of the preceding clauses, wherein the system includes electronics (60) for remote readout of the set of MEMS device and a receiver for inductive powering of the set of MEMS devices.

Clause 10. An assembly (200) comprising layered stack (201,202) of least first (100a) and second ones (100b) of the systems according to any of clause 1-19, wherein layers are arranged so that the pockets (2a) comprised in a first layer (201) are shifted laterally with respect to the pockets (2b) comprised in a second layer (202) of the stack.

Clause 11. A clothing product (300) comprising the system according to any of clauses 1-9.

Clause 12. A diagnostic product (400) for measuring a vital sign of a subject (1000) comprising the system (100) according to any of clauses 1-9, or the assembly according to clause 10.

Clause 13. The diagnostic product according to clause 12, wherein the product is a compression bandage (401), a bedding product (402) or a seating product.

Clause 14. A method (500) of manufacturing a system (100) for measuring an external force, comprising: printing (501) electroconductive wiring (5) to for a circuit along a sheet (9) comprising a thermoplastic elastomer composition and connecting (502) a MEMS device (4) to the circuit; thermoforming (503) a second sheet (11) comprising a thermoplastic elastomer composition to form an outwards protruding shape; laminating the sheets (8,9) placed over each other to form a closed pocket (2) with an outwardly protruding shape, the pocket enclosing the MEMS device.

Clause 15. The method according to clause 14, wherein an intermediate sheet (13) comprising a thermoplastic elastomer composition is laminated between the first sheet (9) and the second sheet (11), the intermediate sheet (13) patterned to include apertures (6a,7a) at positions in accordance with a main volume (6) and an adjacent volume (7) of the pocket (2), whereby the protruding shape is exclusively above the main volume and the MEMS device is at least in part positioned in the adjacent volume.

The invention claimed is:

1. A system for measuring an external force, the system comprising:
a flexible substrate comprising one or more elastomeric compositions forming a set of closed gas filled pockets, wherein each pocket, of the set of closed gas filled pockets, has a flexible wall that deforms as a function of the external force on the flexible wall;
a set of micro-electromechanical system devices, wherein each MEMS device, of the set of MEMS devices, is configured to cause variation of an electric signal as a function of a pressure inside a respective pocket of the set of closed gas filled pockets,
wherein the flexible wall has an outwards protruding shape configured to flex, in response to an increase of the external force, inwards into the pocket for increasing a pressure inside the pocket, and
wherein the flexible wall comprises a shape recovering resilient composition configured to cause the flexible wall to resiliently recover, in response to a decrease of the external force while the flexible wall is flexing inwards, to the outwards protruding shape.

2. The system according to claim 1, wherein the flexible substrate comprises a stack of two or more thermoplastic elastomer sheets including:
a first sheet forming a sensing layer of the flexible substrate that includes the flexible wall, and
a second sheet forming a base layer opposite the sensing layer, and wherein the pockets are formed between the sensing layer and the base layer.

3. The system according to claim 2, wherein the two or more thermoplastic elastomer sheets include a structured intermediate sheet forming a spacer structure between the sensing layer and the base layer with an upstanding wall structure forming sidewalls that laterally bound the pockets and separate pockets from adjacent pockets.

4. The system according to claim 3, wherein the pocket comprises a main volume in fluid connection to an adjacent volume protruding sideways from the main volume, wherein the outwards protruding shape in the flexible wall is formed exclusively above the main volume, and
wherein the MEMS device is at least in part disposed in the adjacent volume.

5. The system according to claim 4, wherein the adjacent volume is formed in the sidewall of the pocket.

6. The system according to claim 1, wherein the system comprises a reference pressure sensor positioned outside the pocket.

7. The system according to claim 1, wherein a predominant portion of an exterior surface of the outwards protruding shape extends parallel along the base layer.

8. The system according to claim 1, wherein the flexible substrate includes one or more thermoplastic elastomer compositions.

9. The system according to claim 1, wherein the system is configured to receive a reference pressure from an external device that is paired with the system.

10. The system according to claim 1, wherein the system includes:
electronics for remote readout of the set of MEMS devices, and
a receiver for inductive powering of the set of MEMS devices.

11. The system according to claim 1, wherein the plurality of pockets are arranged in an array, and
wherein each pocket, of the plurality of pockets, is spaced from adjacent pockets in the array, such that a globally applied external force acting upon the system is distributed as a plurality of external forces acting upon individual ones of the pockets arranged in the array.

12. The system according to claim 1 forming an assembly comprising a layered stack of flexible substrates forming respective sets of pockets with respective MEMS devices, wherein respective layers of the layered stack are arranged so that pockets comprised in a first layer of the layered stack are shifted laterally with respect to pockets comprised in a second layer of the layered stack.

13. The system according to claim 1 forming part of a clothing product.

14. The system according to claim 1 forming part of a diagnostic product.

15. The system according to claim 14, wherein the diagnostic product is a product taken from the group consisting of: a compression bandage, a bedding product, a seating product, an underlayment for a compression bandage, a bedding product, and a seating product.

16. A method of using the system of claim 1 to perform monitoring a pressure between a body part and a bandage applied thereto, the method comprising:

positioning the system between the body part and the bandage, and monitoring the electric signal output of at least one MEMS device of the system as a function of time.

17. The method according to claim 16, further comprising determining whether the signal corresponds to a pressure outside a specified pressure range.

18. The method according to claim 17, wherein the specified pressure range is 10 to 70 mbar.

19. The method according to claim 16, comprising monitoring a plurality of electric signal outputs of respective MEMS devices comprised in individual pockets of the set of closed gas pockets.

20. A method of manufacturing a system for measuring an external force, the method comprising printing electroconductive wiring for a circuit along a sheet comprising a thermoplastic elastomer composition and connecting a set of micro-electromechanical system devices to the circuit;

thermoforming a second sheet comprising a thermoplastic elastomer composition to form an outwards protruding shape;

laminating the sheets placed over each other to form a set of closed gas filled pocket with an outwardly protruding shape, the set of pockets enclosing the set of MEMs devices, wherein each MEMS device, of the set of MEMS devices, is configured to cause variation of an electric signal as a function of a pressure inside a respective pocket of the set of closed gas filled pockets, wherein the flexible wall has an outwards protruding shape configured to flex, in response to an increase of the external force, inwards into the pocket for increasing a pressure inside the pocket, and wherein the flexible wall comprises a shape recovering resilient composition configured to cause the flexible wall to resiliently recover, in response to a decrease of the external force while the flexible wall is flexing inwards, to the outwards protruding shape.

21. The method according to claim 20, wherein an intermediate sheet comprising a thermoplastic elastomer composition is laminated between the first sheet and the second sheet, the intermediate sheet patterned to include apertures at positions in accordance with a main volume and an adjacent volume of the pocket, whereby the protruding shape is exclusively above the main volume and the MEMS device is at least in part positioned in the adjacent volume.

\* \* \* \* \*